(12) United States Patent
Andino-Pavlovsky et al.

(10) Patent No.: US 7,390,646 B2
(45) Date of Patent: Jun. 24, 2008

(54) BACTERIAL VECTORS AND METHODS OF USE THEREOF

(75) Inventors: Raul Andino-Pavlovsky, San Francisco, CA (US); Marco Vignuzzi, San Francisco, CA (US); Derek H. Wells, Palo Alto, CA (US)

(73) Assignee: The Regents of the University of California, Oakland, CA (US)

( * ) Notice: Subject to any disclaimer, the term of this patent is extended or adjusted under 35 U.S.C. 154(b) by 144 days.

(21) Appl. No.: 10/944,256

(22) Filed: Sep. 17, 2004

(65) Prior Publication Data

US 2005/0118193 A1   Jun. 2, 2005

Related U.S. Application Data

(60) Provisional application No. 60/504,647, filed on Sep. 17, 2003.

(51) Int. Cl.
*C12N 1/21* (2006.01)
*C12P 21/00* (2006.01)

(52) U.S. Cl. .............................. 435/252.33; 435/252.3; 435/69.1

(58) Field of Classification Search ...................... None
See application file for complete search history.

(56) References Cited

U.S. PATENT DOCUMENTS

| | | | |
|---|---|---|---|
| 6,383,496 B1 * | 5/2002 | Curtiss et al. | 424/200.1 |
| 6,475,482 B1 | 11/2002 | Bermudes et al. | |
| 2002/0045587 A1 | 4/2002 | Goebel | |
| 2002/0086032 A1 | 7/2002 | Mahan et al. | |
| 2003/0170211 A1 | 9/2003 | Goudsmit et al. | |
| 2004/0115221 A1 | 6/2004 | Portnoy et al. | |

FOREIGN PATENT DOCUMENTS

| WO | WO 96/40238 | | 12/1996 |
|---|---|---|---|
| WO | WO 02/26251 | * | 4/2002 |

OTHER PUBLICATIONS

Verma et al., Nature, 389:239-242, 1997.*
Palu et al., J. Biotechnol., 68:1-13, 1999.*
Wadhwa et al., Mutation Research 567: 71-84, 2004.*
Branch, TIBS 23: 45-50, 1998.*
Fox, web site: http://news.yahoo.com/news?tmpl—story2&cid=570 &u=/nm/2003/sc_nm/health_genetherapy_dc&:printer-1.*
Beuzon et al. (2000) *EMBO Journal*. 19:3235-3249.
Brumell et al. (2001) *Cellular Microbiology* 3:75-84.
Crotty et al. (1999) *Journal of Virology* 73:9485-95.
Crotty et al.(2001) *Journal of Virology* 75:7435-7452.
Dietrich et al. (1999) *Immunology Today* 20:251-53.
Dietrich (1998) *Nature Biotechnology* 16:181-185.
Nichols et al. (1995) *Annals of the New York Academy of Sciences*. 772:30-9.
Forbes et al. (2003) *Cancer Res*. 63:5188-5193.
Pawelek et al. (2003) *Lancet Oncol*. 4:548-556.

* cited by examiner

*Primary Examiner*—Nancy Vogel
(74) *Attorney, Agent, or Firm*—Paula A. Borden; Bozicevic, Field & Francis LLP

(57) ABSTRACT

The present invention provides a live, attenuated, invasive bacterium that infects a mammalian host cell, and releases exogenous RNA into the cytoplasm of the host cell. The present invention further provides compositions, including immunogenic compositions, comprising a subject bacterium. The present invention provides methods of delivering an RNA to a eukaryotic host cell in vitro, ex vivo, or in vivo. The present invention provides methods of delivering a protein to a host cell in vitro, ex vivo, or in vivo. The present invention provides methods of controlling expression of a target gene in a eukaryotic host cell. The present invention provides methods of inducing an immune response in a mammalian host to a polypeptide antigen, the method involving administering to the host a subject bacterium, wherein the antigen is encoded by the exogenous RNA produced by the bacterium.

33 Claims, 2 Drawing Sheets

1 2 3 4

T7 RNA pol ——

US 7,390,646 B2

BACTERIAL VECTORS AND METHODS OF USE THEREOF

CROSS-REFERENCE

This application claims the benefit of U.S. Provisional Patent Application No. 60/504,647, filed Sep. 17, 2003, which application is incorporated herein by reference in its entirety.

STATEMENT REGARDING FEDERALLY SPONSORED RESEARCH

The U.S. government may have certain rights in this invention, pursuant to grant Nos. PO1Ai46007 awarded by the National Institutes of Health.

FIELD OF THE INVENTION

This invention is in the field of bacterial delivery systems for delivering gene products, e.g., RNA and proteins, in vivo.

BACKGROUND OF THE INVENTION

The delivery of gene products, such as RNA and proteins, to animals or animal cells is desirable for a variety of applications. Such applications include therapy of acquired or inherited diseases or conditions, induction of an immune response to a protein antigen, the study of various cellular functions, etc.

DNA-based methods of delivering gene products to animals and animal cells have been developed. DNA vectors are relatively easy to engineer, and are genetically stable. However, DNA vectors cannot replicate nor propagate in host cells, and as such are not optimal for delivery of gene products to cells. Furthermore, there are concerns regarding integration of exogenous DNA into the genome of a host cell, which has the potential to cause undesirable genetic alterations in the host cell.

There is a need in the art for improved methods of delivering gene products, such as RNA and protein, to eukaryotic cells and organisms, e.g., to animals and animal cells. The present invention addresses this need.

Literature

Published U.S. patent application Nos. 20020045587, 20030170211, 20040115221, and 20020086032; Beuzon et al. (2000) *EMBO Journal.* 19:3235-3249; Brumell et al. (2001) *Cellular Microbiology* 3:75-84; Crotty et al. (1999) *Journal of Virology* 73:9485-95; Crotty et al.(2001) *Journal of Virology* 75:7435-7452; Dietrich et al. (1999) *Immunology Today* 20:251-53; Dietrich (1998) *Nature Biotechnology* 16:181-185; Nichols et al. (1995) *Annals of the New York Academy of Sciences.* 772:30-9; U.S. Pat. No. 6,475,482; WO 96/40238; Forbes et al. (2003) *Cancer Res.* 63:5188-5193; Pawelek et al. (2003) *Lancet Oncol.* 4:548-556.

SUMMARY OF THE INVENTION

The present invention provides a live, attenuated, invasive bacterium that infects a mammalian host cell, and releases exogenous RNA into the cytoplasm of the host cell. The present invention further provides compositions, including immunogenic compositions, comprising a subject bacterium. The present invention provides methods of delivering an RNA to a eukaryotic host cell in vitro, ex vivo, or in vivo. The present invention provides methods of delivering a protein to a host cell in vitro, ex vivo, or in vivo. The present invention provides methods of controlling expression of a target gene in a eukaryotic host cell. The present invention provides methods of inducing an immune response in a mammalian host to a polypeptide antigen, the method involving administering to the host a subject bacterium, wherein the antigen is encoded by the exogenous RNA produced by the bacterium.

DEFINITIONS

Figure 1:
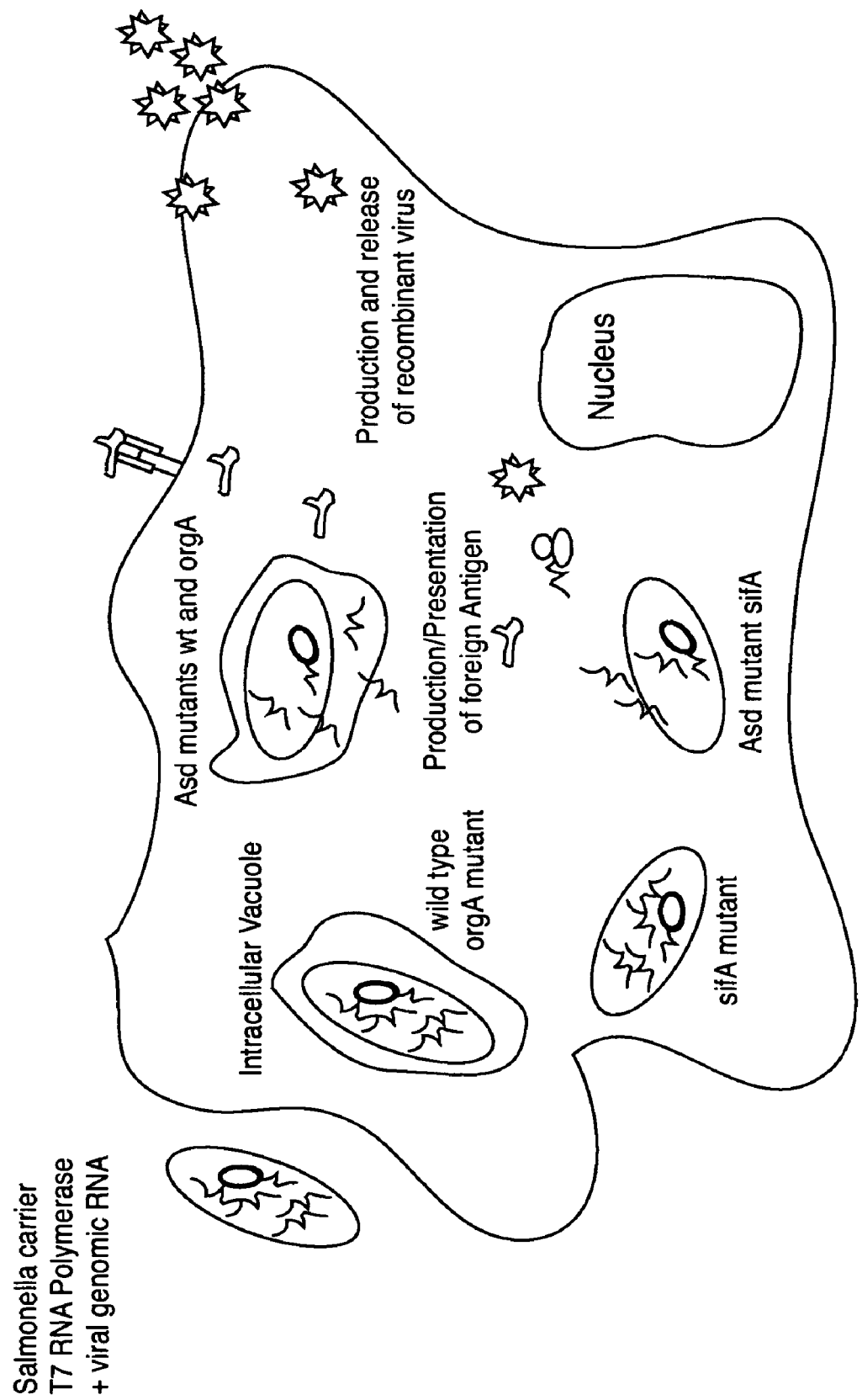
FIG. 1 depicts schematically an exemplary embodiment of a subject bacterial delivery system.

The terms "polynucleotide" and "nucleic acid", used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

A "small interfering" or "short interfering RNA" or siRNA is a RNA duplex of nucleotides that is targeted to a gene of interest (a "target gene"). An "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29 nucleotides, 28 nucleotides, 27 nucleotides, 26 nucleotides, 25 nucleotides, 24 nucleotides, 23 nucleotides, 22 nucleotides, 21 nucleotides, 20 nucleotides, 19 nucleotides, 18 nucleotides, 17 nucleotides, 16 nucleotides, 15 nucleotides, 14 nucleotides, 13 nucleotides, 12 nucleotides, 11 nucleotides, or 10 nucleotides in length. In some embodiments, the length of the duplex is 19-25 nucleotides in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5 nucleotides, 6 nucleotides, 7 nucleotides, 8 nucleotides, 9 nucleotides, 10 nucleotides, 11 nucleotides, 12 nucleotides, or 13 nucleotides in length. The hairpin structure can also contain 3' or 5' overhang portions. The 3' or 5' overhang is from 1 nucleotide to about 100 nucleotides in length, e.g., from about 1 nucleotide to about 5 nucleotides, from about 5 nucleotides to about 10 nucleotides, from about 10 nucleotides to about 15 nucleotides, from about 15 nucleotides to about 20 nucleotides, from about 20 nucleotides to about 25 nucleotides, from about 25 nucleotides to about 30 nucleotides, from about 30 nucleotides to about 40 nucleotides, from about 40 nucleotides to about 50 nucleotides, from about 50 nucleotides to about 60 nucleotides, from about 60 nucleotides to about 75 nucleotides, or from about 75 nucleotides to about 100 nucleotides in length. In some embodiments, the overhang is a 3' or a 5' overhang 1 nucleotides, 2 nucleotides, 3 nucleotides, 4 nucleotides, or 5 nucleotides in length.

The terms "peptide," "oligopeptide," "polypeptide," "polyprotein," and "protein" are used interchangeably herein, and refer to a polymeric form of amino acids of any length, which can include coded and non-coded amino acids, chemically or biochemically modified or derivatized amino acids, and polypeptides having modified peptide backbones.

"Recombinant," as used herein, means that a particular DNA or RNA sequence is the product of various combinations of cloning, restriction, and/or ligation steps resulting in a construct having a structural coding or non-coding sequence distinguishable from homologous sequences found in natural systems. Generally, DNA sequences encoding the structural coding sequence can be assembled from cDNA fragments and short oligonucleotide linkers, or from a series of oligonucleotides, to provide a synthetic gene which is capable of being expressed in a recombinant transcriptional unit. Such sequences can be provided in the form of an open reading frame uninterrupted by internal nontranslated sequences, or introns, which are typically present in eukaryotic genes. Genomic DNA comprising the relevant sequences could also be used. Sequences of non-translated DNA may be present 5' or 3' from the open reading frame, where such sequences do not interfere with manipulation or expression of the coding regions.

Thus, e.g., the term "recombinant" polynucleotide or nucleic acid refers to one which is not naturally occurring, or is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. The term "recombinant" virus or viral RNA refers to one which is not naturally occurring, or is made by the artificial combination of two or more otherwise distinct viruses. This artificial combination is often accomplished by either chemical synthesis means, or by the artificial manipulation of isolated segments of nucleic acids, e.g., by genetic engineering techniques.

By "construct" is meant a recombinant nucleic acid, generally recombinant DNA, which has been generated for the purpose of the expression of a specific nucleotide sequence(s), or is to be used in the construction of other recombinant nucleotide sequences.

Similarly, a "recombinant polypeptide" refers to a polypeptide or polyprotein which is not naturally occurring, or is made by the artificial combination of two otherwise separated segments of amino acid sequences. This artificial combination may be accomplished by standard techniques of recombinant DNA technology, such as described above, i.e., a recombinant polypeptide may be encoded by a recombinant polynucleotide. Thus, a recombinant polypeptide is an amino acid sequence encoded by all or a portion of a recombinant polynucleotide.

As used herein, the term "exogenous polypeptide" includes a polypeptide that is not normally produced by a given organism or cell, e.g., a bacterium, a virus, or a cell, in nature. As used herein, the term "exogenous polypeptide" includes polypeptides that a eukaryotic host cell does not normally synthesize; polypeptides that a eukaryotic host cell is capable of synthesizing, but does so only at low levels; and polypeptides that are similar to an endogenous polypeptide that a eukaryotic host cell produces. For example, the eukaryotic host cell may produce an endogenous protein, but the endogenous protein that is produced is non-functional, while the exogenous polypeptide is a functional variant of the non-functional endogenous polypeptide. The term "endogenous" polypeptide refers to a polypeptide that is normally produced by a given organism or cell in nature.

The terms "exogenous RNA" and "heterologous RNA" are used interchangeably herein, and include to an RNA that is not normally present in a bacterial or eukaryotic cell (e.g., that is nor normally produced by a given bacterium, organism, or eukaryotic cell in nature); an RNA that is introduced into a eukaryotic cell using a subject bacterial delivery system; an RNA that is produced in a eukaryotic cell, but only at low levels; and a variant of an endogenous RNA that is produced by a eukaryotic cell. The term "endogenous" nucleic acid (or gene) refers to a nucleic acid (e.g., a polynucleotide comprising a nucleotide sequence encoding an RNA and/or a polypeptide) that is normally present within the genome of an organism or cell.

"Operably linked" refers to a juxtaposition wherein the components so described are in a relationship permitting them to function in their intended manner. For instance, a promoter is operably linked to a coding sequence if the promoter affects its transcription or expression. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

The term "host cell," as used herein, refers to in vivo, ex vivo, or in vitro eukaryotic cells or cell lines cultured as unicellular entities, which eukaryotic cells can be, or have been, used as recipients for a subject bacterial vector, and include the progeny of the original cell which has been genetically modified by the bacterial vector. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a subject bacterial vector. Similarly, a subject bacteria is a genetically modified bacterium, by virtue of introduction into a suitable bacterium an exogenous DNA, e.g., a DNA that is foreign to the bacterium.

As used herein, "invasive bacteria" are bacteria that are capable of delivering exogenous RNA to animal cells or animal tissue. "Invasive bacteria" include bacteria that are naturally capable of entering the cytoplasm of eukaryotic cells (e.g., animal cells), as well as bacteria that are genetically engineered to enter the cytoplasm of eukaryotic cells or cells in the tissue of a eukaryotic organism.

As used herein, "attenuated, invasive bacteria" are invasive bacteria as defined herein which are capable of infecting an animal host without establishing a productive infection and/or causing disease in the infected host. Thus, at most an attenuated bacterial strain may cause a self-limiting, clinically insignificant infection.

As used herein the term "isolated" is meant to describe a polynucleotide, a polypeptide, or a cell that is in an environment different from that in which the polynucleotide, the polypeptide, or the cell naturally occurs.

As used herein, "an immune response" is meant to encompass cellular and/or humoral immune responses that are sufficient to inhibit, limit, or prevent infection, or prevent, limit, or inhibit onset of disease symptoms caused by a microbial organism, particularly a pathogenic microbial organism, and/or to inhibit, reduce, or prevent proliferation of a tumor cell, and/or to reduce tumor cell numbers or tumor mass, and/or to reduce the likelihood that a tumor will form. The terms "mucosal immune response" and "mucosal immunity" is a term well understood in the art, and refers to an immune response characterized by production of secretory IgA in mucosal tissues such as gastrointestinal tract tissues, including rectal tissues, and tissues of the lower gastrointestinal tract (e.g., intestinal tissues, such as intestinal tissues where Peyer's patches are found); vaginal tissues; and tissues of the respiratory tract. A mucosal immune response may also be characterized by induction of a cellular immune response and/or an inflammatory response.

The terms "cancer," "neoplasm," and "tumor" are used interchangeably herein to refer to cells which exhibit relatively autonomous growth, so that they exhibit an aberrant growth phenotype characterized by a significant loss of control of cell proliferation. Cancerous cells can be benign or malignant.

The terms "subject," "individual," "host," and "patient" are used interchangeably herein to refer to any subject, particularly a mammalian subject, for whom diagnosis or therapy is desired, particularly humans. Other subjects may include cattle, dogs, cats, guinea pigs, rabbits, rats, mice, non-human primates, horses, and so on.

The terms "treatment," "treating," and the like are used herein to generally refer to obtaining a desired pharmacologic or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, e.g., a human, and includes: (a) preventing the disease from occurring in a subject which may be predisposed to the disease but has not yet been diagnosed as having it, e.g., reducing the risk that an individual will develop the disease, reducing the severity of a disease symptom; (b) inhibiting the disease, i.e., arresting its development; and (c) relieving the disease, i.e., causing regression of the disease. In some embodiments, the invention is directed toward reducing or preventing a disease caused by a pathogenic organism. In these embodiments, "treatment" can include reducing the severity of a disease after infection with a pathogenic organism.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a bacterium" includes a plurality of such bacteria and reference to "the immunogenic composition" includes reference to one or more compositions and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides a live, attenuated, invasive bacterium that comprises exogenous RNA, wherein the bacterium infects a eukaryotic host cell, and releases exogenous RNA into the cytoplasm of the host cell. The present invention further provides compositions, including immunogenic compositions, comprising a subject bacterium. The present invention provides methods of delivering an RNA to a eukaryotic host cell in vitro, ex vivo, or in vivo. The present invention provides methods of delivering a protein to a host cell in vitro, ex vivo, or in vivo. The present invention provides methods of controlling expression of a target gene in a eukaryotic host cell. The present invention provides methods of inducing an immune response in a mammalian host to a polypeptide antigen, the method involving administering to the host a subject bacterium, wherein the antigen is encoded by the exogenous RNA produced by the bacterium.

The present invention provides a live, attenuated, invasive bacterium that comprises an exogenous DNA that encodes exogenous RNA, and compositions comprising the bacterium. A subject bacterium produces the exogenous RNA within the bacterial cell in vitro (e.g., during in vitro cell culture), after entry of the bacterial cell into the host eukaryotic cell, or both during in vitro cell culture and after entry into the host eukaryotic cell.

Following infection of a eukaryotic host cell, the bacterium releases the exogenous RNA into the cytoplasm of the host cell. A subject bacterium is thus a bacterial delivery system for delivering RNA to a host eukaryotic cell, e.g., a mammalian cell. Suitable RNA includes a viral RNA genome; an RNA that is a portion of a viral RNA genome; interfering RNA (RNAi); small (or short) interfering RNA (siRNA) (see, e.g., Semizarov et al. (2003) Proc. Natl. Acad. Sci. USA 100:6347-6352; Elbashir et al. (2001) Nature 411:494-498; U.S. Pat. No. 6,506,559); a ribozymes; an antisense RNA; double-stranded RNA (dsRNA); an mRNA encoding a protein; and the like.

In some embodiments, a subject bacterium provides for delivery of a protein to a eukaryotic host cell. Thus, e.g., a subject bacterium is useful for delivering exogenous RNA to a eukaryotic host cell, wherein the exogenous RNA comprises a nucleotide sequence that encodes one or more proteins, and wherein the RNA is capable of being translated in the host cell. In some embodiments, the RNA is produced within the bacterial cell during in vitro cell culture. In other embodiments, the RNA is produced within the bacterial cell after the bacteria enters the eukaryotic host cell. In other embodiments, the RNA is produced within the bacterial cell both during in vitro culture and after the bacteria enters the eukaryotic host cell.

In the host cell, the RNA that was produced by the bacterium during in vitro culture, and/or that was produced in the bacterial cell following entry of the bacterial cell into the eukaryotic cell, is released into the cytoplasm of the host cell, and is translated in the host cell. Thus, the host cell produces the exogenous polypeptide encoded by the exogenous RNA. In some embodiments, the exogenous polypeptide is a therapeutic polypeptide. In some embodiments, the exogenous polypeptide stimulates an immune response or modulates an immune function. Where the exogenous polypeptide corresponds to a polypeptide of a pathogenic microorganism (e.g., a pathogenic virus), an immune response to the pathogenic microorganism is elicited. Where the exogenous RNA and encoded polypeptide(s) correspond to a replication competent viral genome, a virus life cycle is launched that results in the production of more viral RNAs and polypeptides, as well as viral progeny.

In some embodiments, a subject bacterial delivery system comprises a live, attenuated bacterium (e.g., a *Salmonella* bacterium or other suitable bacterial strain) comprising an exogenous DNA operably linked to a promoter that is recognized by an RNA polymerase, where the exogenous DNA encodes an exogenous RNA. In many embodiments, a subject bacterium is further genetically modified to comprise a nucleic acid that encodes an RNA polymerase. In some embodiments, the RNA polymerase is under the control of an inducible promoter.

As one non-limiting example, a subject bacterium is genetically modified to include a nucleic acid that comprises a nucleotide sequence encoding bacteriophage T7 RNA polymerase under the control of an inducible promoter. The bacterium is cultured in vitro (e.g., in culture medium, without a eukaryotic host cell); inducer is added, which induces production of the T7 RNA polymerase; the exogenous DNA is transcribed by the T7 RNA polymerase; and exogenous RNA is produced.

The present invention provides distinct advantages over previously described bacterial delivery systems. There is no requirement for replication (cell division) of the bacterium following infection of the eukaryotic host cell. Because the exogenous RNA is synthesized in the bacterium in vitro and/or within the bacterium following entry of the bacterium into the eukaryotic host cell, the bacterium contains multiple copies of the exogenous RNA. The bacterium need only infect a eukaryotic host cell, and once inside the host cell, the bacterium releases the exogenous RNA into the cytoplasm of the host cell.

In some embodiments, the exogenous RNA being delivered is viral RNA. In these embodiments, because the nucleic acids delivered by the bacterium are infectious RNAs, rather than DNA expression plasmids, a viral replication cycle will be launched in the host cell that will not only greatly amplify the number of RNAs (e.g., transcripts encoding the exogenous polypeptides, or RNAs that control gene expression) but will also permit production of progeny virus that can further infect neighboring cells and in turn augment the overall production of the protein.

Furthermore, cases of DNA integration have been described for *Salmonella*-DNA plasmid delivery systems, which integration events have been attributed to the high copy number plasmids required for production of large amounts of protein. In contrast, the plasmids used to genetically modify a bacterium in the present system are low or single copy plasmids, since the present RNA delivery system and method relies on the delivery of infectious RNA molecules transcribed within the bacteria from a single DNA plasmid. Thus, the instant delivery system is substantially free of integration events.

As noted above, a subject bacterial delivery system provides for delivery of multiple copies of an exogenous RNA to a host eukaryotic (e.g., mammalian) cell. In some embodiments, the exogenous RNA being delivered encodes an antigen(s). In these embodiments, a subject bacterial system provides for production of amounts of the encoded antigen effective to induce an immune response to the antigen. In other embodiments, the exogenous RNA being delivered encodes a therapeutic protein. In these embodiments, a subject bacterial vector system provides for production in the mammalian host cell of the therapeutic protein in an amount effective to exert a therapeutic effect. In other embodiments, the exogenous RNA being delivered is an RNA that controls host cell gene expression by inhibiting expression of a target gene within the mammalian host. In these embodiments, a subject bacterial vector system provides for delivery of an RNA in an amount effective to inhibit expression of a target gene.

Bacterial Vectors

The present invention provides a live, attenuated, invasive bacterium that comprises an exogenous DNA encoding exogenous RNA; and compositions comprising the bacterium. The present invention provides a live, attenuated, invasive bacterium that synthesizes exogenous RNA in vitro, and/or after entry into a eukaryotic host cell, and releases the synthesized exogenous RNA into the cytoplasm of a eukaryotic host cell (e.g., a mammalian host cell) following infection of the host cell; and compositions comprising the bacterium.

A subject genetically modified bacterium is genetically modified by introducing into the bacterium a DNA construct (also referred to as a "DNA expression vector") that comprises, from 5' to 3', one or more control elements, and a nucleotide sequence encoding an exogenous RNA, where the control element(s) is operably linked to the exogenous RNA-encoding nucleotide sequence. Control elements include a promoter that is functional in the bacterium such that during in vitro culture or after the bacterium has entered the eukaryotic cell, the DNA is transcribed, and exogenous RNA is produced within the bacterium.

In many embodiments, the DNA construct is a plasmid. In many embodiments, the plasmid is a single-copy plasmid. In other embodiments, the plasmid is a low copy number plasmid, e.g., each bacterium comprises two to ten copies of the plasmid, e.g., from two copies to about 5 copies, or from about 5 copies to about 10 copies, of the plasmid. In other embodiments, the plasmid is a high copy number plasmid, e.g., each bacterium comprises from about 100 to about 200 copies of the plasmid.

In other embodiments, the exogenous DNA encoding exogenous RNA is integrated into the bacterial genome. In these embodiments, an exogenous RNA-encoding nucleotide sequence is operably linked to one or more control elements (e.g., a promoter), and is integrated into the bacterial genome.

A subject bacterial delivery system comprises a subject bacterium which has been cultured in vitro for a suitable period of time such that exogenous RNA encoded by the DNA construct is produced within the bacterial cell, or a subject bacterium that synthesizes an exogenous RNA following entry into a eukaryotic host cell. A subject bacterial delivery system comprises from about 10 copies to about $10^9$ copies of the exogenous RNA encoded by the DNA construct, e.g., from about 10 to about $10^2$, from about $10^2$ to about $10^4$, from about $10^4$ to about $10^6$, from about $10^6$ to about $10^7$, from about $10^7$ to about $10^8$, or from about $10^8$ to about $10^9$ copies, or more, of the exogenous RNA per bacterium. A subject bacterial delivery system is administered contacted with eukaryotic cells in vitro, ex vivo, or in vivo, such that the bacteria enter the cytoplasm of the eukaryotic host cells, and deliver the RNA synthesized in in vitro cell culture and/or following entry of the bacterium into the host cell, into the cytoplasm of the host cells.

Bacterial Libraries

The present invention further provides a population (e.g., a "library") of genetically modified bacteria; and compositions comprising a subject bacterial population. The population of bacteria comprises at least two member bacteria, each of which member bacteria produces a different RNA. As used herein, the term "different RNA" refers to the fact that the at least two different RNAs are non-identical in nucleotide sequence. Two different, non-identical RNAs will in some embodiments include overlapping nucleotide sequences; in other embodiments, two non-identical RNAs will have essentially no overlapping nucleotide sequences (e.g., the nucleotide sequences of the two different RNAs will not share significant sequence identity over a stretch of, e.g., 25 nucleotides, 50 nucleotides, or 100 nucleotides).

In some embodiments, a subject population (e.g., a "library") comprises genetically modified bacteria, as described above, which produce RNA comprising nucleotide sequences encoding at least two different polypeptides. In other embodiments, the population produces RNA comprising nucleotide sequences encoding at least three different polypeptides. In other embodiments, the population produces RNA comprising nucleotide sequences encoding at least four different polypeptides. In still other embodiments, the population produces RNA comprising nucleotide sequences encoding more than four different polypeptides. The encoded polypeptides are from about 4 amino acids to about 400 amino acids in length. The population of bacteria comprises at least two member bacteria (e.g., two member bacteria, three member bacteria, four member bacteria, five member bacteria, six member bacteria, etc.) each of which member bacteria produces an RNA comprising a nucleotide sequence encoding one polypeptide. The population comprises two, three, four, five, six, seven, eight, nine, ten, or more, member bacteria, each producing an RNA comprising nucleotide sequences encoding a different polypeptide. Multiple copies of each member bacteria are typically present in the population.

Exogenous polypeptides encoded by exogenous RNA in members of the bacterial population can be any length consistent with their intended use. In some embodiments, exogenous polypeptides are from about 4 to about 6, from about 6 to about 10, from about 10 to about 15, from about 15 to about 20, from about 20 to about 25, from about 25 to about 50, from about 50 to about 75, from about 75 to about 100, from about 100 to about 125, from about 125 to about 150, from about 150 to about 175, from about 175 to about 200, from about 200 to about 225, from about 250 to about 300, from about 300 to about 350, or from about 350 to about 400 amino acids in length. For example, the exogenous polypeptides can be from about four to about 100, from about 100 to about 250, or from about 250 to about 400 amino acids in length.

The present invention further provides a population (e.g., a "library") of genetically modified bacteria, wherein the population comprises genetically modified bacteria, as described above, which produce at least two different RNA that control expression of a target gene. In other embodiments, the population produces at least three different RNA that control expression of a target gene. In other embodiments, the population produces at least four different RNA that control expression of a target gene. In still other embodiments, the population produces more than four different RNA that control expression of a target gene. In some embodiments, each different RNA controls expression of a different target gene. In other embodiments, at least two different RNA control expression of the same target gene, but hybridize to different (e.g., non-identical, which may be overlapping or non-overlapping) regions of the target gene. The population of bacteria comprises at least two member bacteria (e.g., two member bacteria, three member bacteria, four member bacteria, five member bacteria, six member bacteria, etc.) each of which member bacteria comprise a different exogenous RNA. Member bacteria are in many embodiments present in multiple copies in the population.

Bacteria

Suitable bacteria for use in the present invention include those that are capable of entering a eukaryotic host cell, e.g., a mammalian host antigen-presenting cell (e.g., a macrophage, a dendritic cell, and the like), a mammalian host intestinal epithelial cell, etc. As such, a subject bacterium is invasive, e.g., it attaches to the eukaryotic host cell and enters the cytoplasm of the host cell.

Suitable bacteria are attenuated, e.g., they do not substantially cause clinical pathology in the host. Suitable bacteria will in many embodiments comprise one or more mutations or other genetic modifications that increase the ability of the bacterium to release RNA into the cytoplasm of the eukaryotic host cell. Suitable bacteria comprise one or more of the following mutations and/or other genetic modifications (resulting in one or more of the following phenotypes): 1) one or more mutations that result in death of the bacterium in the cytoplasm of a host cell, such that, as the bacterium dies, it releases the exogenous RNA into the cytoplasm of a host animal cell; 2) one or more mutations that result in a reduced ability of the bacterium to be retained in a vacuole in the host animal cell; 3) one or more mutations that result in an a reduced ability of the bacterium to induce apoptosis in the host animal cell; 4) one or more mutations that reduce the ability of the bacterium to synthesize a bacterial cell wall; 5) one or more mutations that reduces the ability of the bacterium to replicate within the eukaryotic host cell; 6) a genetic modification to include a nucleotide sequence encoding a protein that lyses the bacterial cell, where the nucleotide sequence is in many embodiments under the control of an inducible promoter that is activated after entry of the bacterium into a eukaryotic host cell; 7) one or more mutations that confer increased stability of RNA and/or DNA in the bacterium, e.g., a mutation that reduces the activity of a RNase and/or a DNase in the bacterium; 8) one or more mutations that increase the ability of the bacterium to enter into the cytoplasm of the eukaryotic cell; 9) one or more mutations that increase the infectivity of the bacterium, e.g., a mutation that increases invasiveness of the bacterium; 10) one or more mutations that reduce the immunogenicity of the bacterium; and the like. In addition, suitable mutations include mutations that alter the bacterial cell wall, resulting in increased release of RNA from the bacterium into the cytoplasm of the eukaryotic host cell, e.g., one or more mutations that reduce production of a component of the bacterial cell wall, or that result in a reduction in the structural integrity of the bacterial cell wall. Such mutations include, but are not limited to, mutations that reduce production of or that alter one or more of a lipopolysaccharide, an outer membrane protein, a K-antigen, and the like, such that the structural integrity of the bacterial cell wall is reduced, and release of RNA from the bacterium into the cytoplasm of the eukaryotic host cell, is increased.

As noted above, in some embodiments, the bacterium is genetically modified to include a nucleotide sequence that encodes a protein that lyses the bacterial cell ("a cytolytic protein"), where the nucleotide sequence is in many embodiments under the control of an inducible promoter that is activated after entry of the bacterium into a eukaryotic host cell. Typically, the cytolytic protein is not one that causes lysis of the eukaryotic host cell. The cytolytic protein is typically one that is not detrimental to any function of the eukaryotic host cell. In many embodiments, the cytolytic protein is not secreted from the bacterial cell. Suitable cytolytic proteins include, but are not limited to, a phospholipase; a hemolysin; a pore-forming toxin (e.g., an alpha-toxin), a cytolysin of a gram-positive bacterium, such as listeriolysin O; streptolysin O; perfringolysin O; a bacteriophage lambda S gene product; a bacteriophage lambda R gene product; and the like. See, e.g., U.S. Patent Publication No. 20040115221. In many embodiments, the cytolytic protein-encoding nucleotide sequence is operably linked to a control element (e.g., a promoter) that is inducible, such that upon entry of the bacterium into the eukaryotic host cell, the promoter is induced. Suitable promoters include, but are not limited to, a pagC promoter, an ssaG promoter, and the like.

Suitable bacteria include, but are not limited to, *Salmonella* spp. *Shigella* spp., *Listeria* spp., *Rickettsia* spp. and enteroinvasive *Escherichia coli*. Any of these strains can be attenuated, if needed, using known methods. In some embodiments, a subject bacterium is a *Salmonella* bacterium. Examples of *Salmonella* strains which can be employed in the present invention include, but are not limited to, *Salmonella typhi* (ATCC No. 7251) and *S. typhimurium* (ATCC No. 13311).

Examples of *Shigella* strains which can be employed in the present invention include, but are not limited to, *Shigella flexneri* 2a (ATCC No. 29903), *Shigella sonnei* (ATCC No. 29930), and *Shigella disenteriae* (ATCC No. 13313). Examples of *Listeria* strains which can be employed in the present invention include *Listeria monocytogenes* (ATCC No. 15313). Examples of *Rickettsia* strains which can be employed in the present invention include *Rickettsia rickettsiae* (ATCC Nos. VR149 and VR891), *Ricketsia prowaseckii* (ATCC No. VR233), *Ricketsia tsutsugamuchi* (ATCC Nos. VR312, VR150 and VR609), *Ricketsia mooseri* (ATCC No. VR144), *Ricketsia sibirica* (ATCC No. VR151). Examples of enteroinvasive *Escherichia* strains which can be employed in the present invention include *Escherichia coli* strains 4608-58, 1184-68, 53638-C-17, 13-80, and 6-81 (Sansonetti et al, Ann. Microbiol. (Inst. Pasteur), 132A:351-355 (1982)).

Examples of additional bacteria which can be genetically engineered to be invasive include, but are not limited to, *Yersinia* spp., *Escherichia* spp., *Klebsiella* spp., *Bordetella* spp., *Neisseria* spp., *Aeromonas* spp., *Francisella* spp., *Corynebacterium* spp., *Citrobacter* spp., *Chlamydia* spp., *Hemophilus* spp., *Brucella* spp., *Mycobacterium* spp., *Legionella* spp., *Bartonella* spp., *Clostridium* spp., *Bifidobacteria* spp., *Campylobacter* spp., *Pasteurella* spp., *Streptococcus* spp., *Staphylococcus* spp., *Pneumococcus* spp., *Bacteroides* spp., *Fusobacteria* spp., *Rhodococcus* spp., *Pseudomonas* spp., *Helicobacter* spp., *Salmonella* spp., *Vibrio* spp., *Bacillus* spp., *Bacillus subtilis*, lactic acid bacteria, and *Erysipelothrix* spp. These organisms can be engineered to mimic the invasion properties of *Shigella* spp., *Listeria* spp., *Rickettsia* spp., or enteroinvasive *E. coli* spp. by inserting genes that enable them to access the cytoplasm of an animal cell.

Suitable bacteria further include one or more mutations in one or more endogenous bacterial genes such that the bacterium dies after infection of a eukaryotic host cell, and releases RNA, produced in the bacterium in vitro (and/or following entry of the bacterium into the eukaryotic host cell), into the cytoplasm of the eukaryotic host cell without damaging the host cell. Such mutations include mutations that affect the viability of the bacterium after it infects the host cell. Suitable viability-reducing mutations include, but are not limited to, those that render the endogenous bacterial gene or encoded product non-functional in such a manner that the bacterium cannot survive in the host cell and dies. For example, mutations in asd result in impaired ability to synthesize a cell wall component. Other suitable mutations include those that induce lysis of the bacterial cell. Other suitable mutations include auxotrophic mutations such as aroA, aroD, gua, and thy.

Additional mutations that are of interest include mutations that affect the ability of the bacterium to induce apoptosis in the animal host cell; and mutations that affect the ability of the bacterium to be retained in a vacuole in the host cell. In some embodiments, a subject bacterium comprises mutations in one or more of orgA, sifA, and asd. In some embodiments, a subject bacterium comprises mutations in orgA, sifA, and asd. For example, a bacterium that comprises a mutation in an orgA has a reduced ability to induce apoptosis in the host cell; a bacterium that comprises a mutation in sifA has reduced retention in a vacuole in a host cell.

Methods of Generating a Subject Bacterium

Methods of introducing a mutation into a bacterial gene are well known in the art. For example, mutations can be introduced into a bacterial gene using non-specific mutagenesis either chemically, using agents such as N-methyl-N'-nitro-N-nitrosoguanidine, or using recombinant DNA techniques; standard genetic techniques, such as Tn10 mutagenesis, P22-mediated transduction, lambda-phage mediated crossover, and conjugational transfer; or site-directed mutagenesis using recombinant DNA techniques.

In some embodiments, a subject bacterium is genetically modified to include an exogenous nucleic acid (a DNA construct) that comprises a nucleotide sequence that encodes an RNA polymerase that is functional in the bacterium, e.g., a bacteriophage RNA polymerase, which RNA polymerase recognizes the promoter that is operably linked to the exogenous RNA-encoding DNA. For example, in some embodiments, a subject bacterium is genetically modified to include a nucleic acid that comprises a nucleotide sequence that encodes T7 RNA polymerase. In some embodiments, the nucleic acid encoding the RNA polymerase is under the control of an inducible promoter.

A subject bacterium is genetically modified to include a DNA encoding an exogenous RNA. Methods of introducing exogenous DNA into bacteria are well known in the art. Methods for introducing an exogenous DNA (a DNA expression vector) into a bacterium include, but are not limited to chromosome or plasmid mobilization (Miller, A Short Course in Bacterial Genetics, Cold Spring Harbor Laboratory Press, Cold Spring Harbor, N.Y. (1992)); bacteriophage-mediated transduction; chemical-mediated transduction (e.g., calcium phosphate mediated); electroporation (Sambrook, Molecular Cloning: A Laboratory Manual, Cold Spring Harbor Laboratory Press, Cold Spring Harbor, N.Y.); and physical transformation techniques.

Recombinant DNA vectors encoding exogenous RNA are generated using well-established recombinant techniques. A DNA that encodes an exogenous RNA is operably linked to a promoter that is functional in a bacterial cell, e.g., a promoter that is recognized by an RNA polymerase within the bacterial host cell such that the exogenous RNA is synthesized in the bacterial cell. As such, the promoter is one that is recognized by an RNA polymerase. In some embodiments, the promoter is one that is recognized by an exogenous RNA polymerase, e.g., a bacteriophage RNA polymerase such as T7 RNA polymerase. In some embodiments, the promoter is an inducible promoter. Where the exogenous nucleic acid encoding the RNA polymerase is under the control of an inducible promoter, inducer is added to culture medium, and the bacterium synthesizes the exogenous RNA in vitro. In some embodiments, the promoter is specific to the particular bacterium, e.g., a *Salmonella*-specific promoter, etc.

In some embodiments, e.g., where the exogenous DNA encodes an RNA that controls gene expression of a target gene in the host mammalian cell, the bacteria is further genetically modified to include an exogenous nucleic acid comprising a nucleotide sequence that encodes an RNAse that processes a long double-stranded (ds) RNA into shorter RNAs. For example, in some embodiments, a subject bacterium is modified to include an exogenous nucleic acid that encodes a long dsRNA, which long dsRNA specifically inhibits expression of a target gene (e.g., an endogenous gene, a viral gene, etc.) in a mammalian cell; and is further modified to include an exogenous nucleic acid that encodes an RNAse III from *E. coli*; and the like. See, e.g., Yang et al. (2002) Proc Natl Acad Sci USA. 99:9942-9947. When the genetically modified bacterium is cultured in vitro, the long ds RNA is synthesized, and is enzymatically cleaved into shorter RNAs by the RNAse III. Other suitable enzymes include the RNAse III-like enzyme Dicer, and Dicer-like proteins (see, e.g., Zamore et al. (2000) *Cell* 101:25-33; Bernstein et al. (2001) *Nature* 409:363-366; Tang et al. (2003) *Genes Dev.* 17:49-63).

In Vitro Culture

In general, a subject bacterium is cultured in vitro, e.g., in culture medium suitable for bacterial cell growth (and in the absence of any mammalian host cell). The bacteria are cultured under conditions and for a suitable period of time to allow for synthesis in the bacteria of the exogenous RNA. Once sufficient quantities of the exogenous RNA are produced, the bacteria are introduced into a subject (as described below), where the bacteria enter host cells in vivo and release the in vitro synthesized RNA. Alternatively, the RNA is harvested from the bacteria.

Bacteria are cultured in vitro for a suitable period of time, e.g, from about 1 hour to about 24 hours, e.g., from to about 1 hour to about 2 hours, from about 2 hours to about 4 hours, from about 4 hours to about 8 hours, from about 8 hours to about 12 hours, from about 12 hours to about 16 hours, or from about 16 hours to about 24 hours, or more. Typically, the bacteria are cultured in a bacterial cell culture medium at a suitable temperature (e.g., about 37° C.). In some embodiments, depending on the DNA construct that encodes the exogenous RNA, an inducer is added to the medium (e.g., where the DNA construct comprises a nucleotide sequence that encodes an exogenous RNA, where the nucleotide sequence is operably linked to an inducible promoter).

Eukaryotic Host Cells

Host cells that are infected with a subject bacterium are eukaryotic cells, including animal cells, particularly mammalian cells (e.g., human cells). Suitable host cells include any eukaryotic cell capable of being infected with a subject bacterium, including phagocytic cells, non-phagocytic cells, pathogenic cells, and diseased cells. Host cells include in vitro cells, ex vivo cells, and in vivo cells. Where the host cells are mammalian cells in vivo, such cells include any cell that is infected with a subject bacterium, including antigen presenting cells (e.g., macrophages, dendritic cells); epithelial cells (e.g., intestinal epithelial cells); muscle cells; liver cells; pancreatic cells; neuronal cells; fibroblasts; tumor cells; leukocytes, such as macrophages, neutrophils, B-cells, T-cells, monocytes; antigen-presenting cells, such as macrophages, dendritic cells, etc.; and the like.

Exogenous RNA

Exogenous RNA of interest includes, but is not limited to, plus-strand viral RNAS; minus-strand viral RNAS; mRNAs; a fragment of a viral RNA genome; interfering RNA (RNAi); small (or short) interfering RNA (siRNA) (see, e.g., Semizarov et al. (2003) Proc. Natl. Acad. Sci. USA 100:6347-6352; Elbashir et al. (2001) Nature 411:494-498; U.S. Pat. No. 6,506,559); a ribozymes; an antisense RNA; double-stranded RNA (dsRNA); and the like. Suitable RNA viral genomes (and fragments thereof) include naturally-occurring RNA viral genomes; recombinant RNA viral genomes; synthetic RNA viral genomes; etc.

In some embodiments, the exogenous RNA is a viral RNA. Exemplary, non-limiting examples of viral RNA are viral RNAs from members of the family Retroviridae, Flaviviridae, Poxviridae, Paramyxoviridae, Picornaviridae, Orthomyxoviridae, positive strand plant viruses, and the like.

In some embodiments, the exogenous RNA is a recombinant viral RNA, e.g., a viral RNA that includes a nucleotide sequence that encodes a heterologous polypeptide, e.g., a polypeptide that is not normally encoded by the RNA virus. Where the exogenous RNA is a viral RNA, the RNA produced in the bacterial cell in vitro (and/or after entry of the bacterium into the eukaryotic host cell) is released into the cytoplasm of the eukaryotic host cell, and the viral RNA is infectious, e.g., progeny of the exogenous viral RNA infects eukaryotic host cells other than the cell which the bacterium enters, e.g., neighboring eukaryotic host cells. The recombinant viral RNA is infectious, and is non-pathogenic toward the host. Thus, in these embodiments, the exogenous RNA is recombinant live virus RNA. Typically, the recombinant viral RNA is a single-stranded RNA+ (ssRNA+) virus that comprises a nucleotide sequence encoding a heterologous polypeptide. Suitable ssRNA+ viruses that can be used to generate a recombinant viral RNA include, but are not limited to, Flaviviridae, e.g., yellow fever virus, pestiviruses (e.g., bovine viral diarrhea virus), hepatitis C virus, etc.; Arenaviridae, e.g., lymphocyte choriomeningitis virus, Lassa fever virus, etc.; Astroviridae, e.g., human astroviruses; Caliciviridae, e.g., Norwalk virus, Norwalk-like viruses, etc.; Nidoviridae, e.g., coronaviruses, ateriviruses, etc.; Picomaviridae, e.g., poliovirus, aphtoviruses (e.g., foot and mouth disease virus), cardioviruses (e.g., Mengo virus), rhinoviruses, Hepatitis A virus, etc.; Togaviridae, e.g., rubivirus, alphaviruses (e.g., Venezuelan equine encephalitis virus, Semliki forest virus, Sindbis virus, etc.; other picoma-like or ss + strand viruses of plants; and the like. In addition, segmented positive strand viral genomes are suitable for use, e.g., Nodaviridae. Furthermore, negative strand viral genomes are in some embodiments suitable for use, e.g., Paramyxoviridae, e.g., Morbilliviruses; Rhabdoviridae, e.g., Lyssaviruses; and Bunyaviridae, e.g., bunyaviruses. In many embodiments, a cDNA copy of a recombinant ssRNA+ virus is used to generate a DNA expression construct, using techniques standard in the art. In some embodiments, the recombinant virus RNA lacks a 5' cap, yet remains infectious.

As one non-limiting example, as depicted schematically in FIG. 1, a *Salmonella* bacterium is genetically modified to express the T7 RNA polymerase gene. The bacterium is transformed with a DNA plasmid containing the cDNA of a genomic viral RNA. The viral RNA is under the transcriptional control of the T7 RNA polymerase promoter and is synthesized by the T7 RNA polymerase within the bacterium. The viral RNA is recombinant, encoding all proteins for genomic replication and viral production, as well as exogenous antigens. The bacterium infects cells via an intracellular vacuole. The orgA mutation inhibits the induction of apoptosis in the host eukaryotic cell. The sifA mutation results in the cytoplasmic localization of the bacterium. The asd mutation abrogates proper bacterial cell wall synthesis. In result, the recombinant viral RNA molecules are released to the cytoplasm, where viral replication of the RNA genomes naturally occurs. The viral RNAs begin RNA replication and result in the expression of viral protein, as well as exogenous antigen. The viral RNAs also result in progeny virus that can exit the host cell to re-infect neighboring cells, and the exogenous polypeptide can be produced in neighboring cells. For example, where the protein is an antigen, the self-replicating viral RNAs also result in progeny virus that can exit the host cell to re-infect neighboring cells and amplify the immune responses.

Exogenous RNAs Encoding Antigenic Proteins

An exogenous RNA will in some embodiments comprise a nucleotide sequence that encodes an antigenic protein(s), such that, when the bacterium enters the cytoplasm of the eukaryotic host cell, the nucleotide sequence encoding the antigen is translated, thereby synthesizing the antigen. A subject bacterium that comprises an exogenous RNA that comprises a nucleotide sequence that encodes an antigenic protein is suitable for stimulating an immune response to the antigenic protein in a mammalian host. The antigenic protein is derived from an autoantigen, an allergen, a tumor-associated antigen, a pathogenic virus, a pathogenic bacterium, a pathogenic protozoan, a pathogenic helminth, or any other pathogenic organism that infects a mammalian host.

As used herein, the term "a nucleic acid encoding an antigenic protein derived from a pathogenic microorganism" includes nucleic acids encoding wild-type antigenic proteins, e.g., a nucleic acid isolated from a pathogenic virus that encodes a viral protein; synthetic nucleic acids generated in the laboratory that encode antigenic proteins that are identical in amino acid sequence to a naturally-occurring antigenic protein; synthetic nucleic acids generated in the laboratory that encode antigenic proteins that differ in amino acid sequence (e.g., by from one amino acid to about 15 amino acids) from a naturally-occurring antigenic protein, but that nonetheless induce an immune response to the corresponding naturally-occurring antigenic protein; synthetic nucleic acids generated in the laboratory that encode fragments of antigenic proteins (e.g., fragments of from about 5 amino acids to about 50 amino acids, which fragments comprises one or more antigenic epitopes), which fragments induce an immune response to the corresponding naturally-occurring antigenic protein; etc.

The antigen is in many embodiments a polypeptide of from about 4 to about 50 amino acids in length, e.g., from about 4 amino acids to about 7 amino acids, from about 7 amino acids to about 10 amino acids, from about 10 amino acids to about 15 amino acids, from about 15 amino acids to about 20 amino acids, from about 20 amino acids to about 25 amino acids, from about 25 amino acids to about 30 amino acids, from about 30 amino acids to about 35 amino acids, from about 35 amino acids to about 40 amino acids, from about 40 amino acids to about 50 amino acids in length, from about 50 amino acids to about 100 amino acids, or from about 100 amino acids to about 150 amino acids in length.

Similarly, an antigenic protein "derived from" a tumor-associated antigen, a pathogenic virus, a pathogenic bacterium, a pathogenic protozoan, a pathogenic helminth, or any other pathogenic microorganism that infects a mammalian host, includes proteins that are identical in amino acid sequence to a naturally-occurring antigenic protein, and proteins that differ in amino acid sequence (e.g., by from one amino acid to about 15 amino acids) from a naturally-occurring antigenic protein, but that nonetheless induce an immune response to the corresponding naturally-occurring antigenic protein; and fragments of antigenic proteins (e.g., fragments of from about 5 amino acids to about 50 amino acids, which fragments comprises one or more antigenic epitopes), which fragments induce an immune response to the corresponding naturally-occurring antigenic protein.

The present invention further provides a population of genetically modified bacteria, wherein the population comprises genetically modified bacteria, as described above, which produce RNA comprising nucleotide sequences encoding at least two different antigenic polypeptides, or fragments thereof, from a pathogenic organism or a tumor. In other embodiments, the population produces RNA comprising nucleotide sequences encoding at least three different antigenic polypeptides, or fragments thereof, from a pathogenic organism or a tumor. In other embodiments, the population produces RNA comprising nucleotide sequences encoding at least four different antigenic polypeptides, or fragments thereof, from a pathogenic organism or TAA. In still other embodiments, the population produces RNA comprising nucleotide sequences encoding more than four different antigenic polypeptides, or fragments thereof, from a pathogenic organism or a tumor. The encoded polypeptides are from about 4 amino acids to about 400 amino acids in length. Each bacterium of the population produces an RNA comprising a nucleotide sequence encoding one antigenic polypeptide. The population comprises two, three, four, five, six, seven, eight, nine, ten, or more, bacteria each producing an RNA comprising nucleotide sequences encoding a different antigenic polypeptide.

Exogenous antigenic polypeptides encoded by exogenous RNA in members of the bacterial population can be any length consistent with their intended use. In some embodiments, exogenous polypeptides are from about 4 to about 6, from about 6 to about 10, from about 10 to about 15, from about 15 to about 20, from about 20 to about 25, from about 25 to about 50, from about 50 to about 75, from about 75 to about 100, from about 100 to about 125, from about 125 to about 150, from about 150 to about 175, from about 175 to about 200, from about 200 to about 225, from about 250 to about 300, from about 300 to about 350, or from about 350 to about 400 amino acids in length. For example, the exogenous antigenic polypeptides can be from about four to about 100, from about 100 to about 250, or from about 250 to about 400 amino acids in length.

Members of the bacterial population will in some embodiments comprise exogenous RNA that comprise nucleotide sequences encoding overlapping polypeptides. Exogenous polypeptides can overlap by about 1, about 5, about 10, about 20, about 25, about 30, about 35, about 40, about 45, about 50, or about 60 amino acids or more, depending, e.g., on the length of the encoded polypeptide.

In some embodiments, the antigenic polypeptides are human immunodeficiency virus (HIV) polypeptides or fragments thereof. In some of these embodiments, the HIV is HIV type-1. In some embodiments, the at least two different antigenic polypeptides, or fragments thereof, are selected from the group consisting of gag, env, pol and nef polypeptides from HIV. In some of these embodiments, the population comprises nucleotide sequences encoding overlapping fragments of the gag, env, pol and nef polypeptides and each fragment has a length from about four amino acids to about 400 amino acids, from about four amino acids to about 100 amino acids, or from about 100 amino acids to about 250 amino acids.

In some embodiments, the population expresses from about 10% to about 25% of the antigenic polypeptides from the pathogenic organism or tumor. In other embodiments, the population expresses from about 25% to about 50% of the antigenic polypeptides from the pathogenic organism or tumor. In still other embodiments, the population expresses from about 50% to about 90% of the antigenic polypeptides from the pathogenic organism or tumor.

In some embodiments, an immune response to an antigenic protein encoded by an exogenous RNA synthesized by a subject modified bacterium will stimulate a protective immune response to a pathogenic organism that displays the antigenic protein or antigenic epitope (or a protein or an epitope that is cross-reactive with the exogenous RNA-encoded antigenic protein or antigenic epitopes) in the mammalian host. In some embodiments, a cytotoxic T lymphocyte (CTL) response to the antigenic protein will be induced in the mammalian host. In other embodiments, a humoral response to the exogenous RNA-encoded antigenic protein will be induced in the mammalian host, such that antibodies specific to the antigenic protein are generated. In many embodiments, a TH1 immune response to the exogenous RNA-encoded antigenic protein will be induced in the mammalian host. Suitable antigenic proteins include tumor-associated antigens, viral antigens, fungal antigens, bacterial antigens, and protozoan antigens; and antigenic fragments thereof. In some embodiments, the antigenic protein is derived from an intracellular pathogen.

Tumor-specific antigens include, but are not limited to, any of the various MAGEs (Melanoma-Associated Antigen E), including MAGE 1 (e.g., GenBank Accession No. M77481), MAGE 2 (e.g., GenBank Accession No. U03735), MAGE 3, MAGE 4, etc.; any of the various tyrosinases; mutant ras; mutant p53 (e.g., GenBank Accession No. X54156 and AA494311); and p97 melanoma antigen (e.g., GenBank Accession No. M12154). Other tumor-specific antigens include the Ras peptide and p53 peptide associated with advanced cancers, the HPV 16/18 and E6/E7 antigens associated with cervical cancers, MUCI1-KLH antigen associated with breast carcinoma (e.g., GenBank Accession No. J03651), CEA (carcinoembryonic antigen) associated with colorectal cancer (e.g., GenBank Accession No. X98311), gp100 (e.g., GenBank Accession No. S73003) or MART1 antigens associated with melanoma, and the PSA antigen associated with prostate cancer (e.g., GenBank Accession No. X14810). The p53 gene sequence is known (See e.g., Harris et al. (1986) Mol. Cell. Biol., 6:4650-4656) and is deposited with GenBank under Accession No. M14694. Thus, the present invention can be used as immunotherapeutics for cancers including, but not limited to, cervical, breast, colorectal, prostate, lung cancers, and for melanomas.

Exogenous polypeptides can be from any of a variety of pathogenic organisms, or from a plurality of pathogenic organisms. Exogenous polypeptides are from pathogenic organisms, including, but not limited to, *Plasmodium* spp.; *Eimeria* spp.; *Schistosoma* spp.; *Trypanosoma* spp.; *Plasmodium* spp.; *Leishmania* spp.; *Cryptosporidia* spp.; *Toxoplasma* spp.; *Pneumocystis* spp.; *Vibrio cholerae*; *Streptococcus pyogenes*; *Neisseria meningitidis*; *Neisseria gonorrhoeae*; *Corynaebacterium diphtheriae*; *Clostridium tetani*; *Branhamella catarrhalis*; *Bordetella pertussis*; *Haemophilus* spp. (e.g., influenzae); *Chlamydia* spp.; Enterotoxigenic *Escherichia coli*; Human Immunodeficiency virus, type I; Human Immunodeficiency virus, type II; Simian Immunodeficiency virus; Human T lymphotropic virus, type I and II; Respiratory syncytial virus; Hepatitis A virus; Hepatitis B virus; Hepatitis C virus; Herpes simplex virus, type I; Herpes simplex virus, type II; Cytomegalovirus; Influenza virus; Parainfluenza virus; Poliovirus; Rotavirus; Coronavirus; Rubella virus; Measles virus; Mumps virus; *Varicella*; Epstein Barr virus; ebola virus; Adenovirus; Papilloma virus; Yellow Fever virus; West Nile Virus; Rabies virus; *Candida* spp. (especially *albicans*); *Cryptococcus* spp. (especially *neoformans*); *Blastomyces* spp. (*dermatitidis*); *Histoplasma* spp. (especially *capsulatum*); *Coccidioides* spp. (especially *immitis*); *Paracoccidioides* spp. (especially *brasiliensis*); and *Aspergillus* spp.

Viral antigens are derived from known causative agents responsible for diseases including, but not limited to, measles, mumps, rubella, poliomyelitis, hepatitis A, B (e.g., GenBank Accession No. E02707), and C (e.g., GenBank Accession No. E06890), as well as other hepatitis viruses, influenza, adenovirus (e.g., types 4 and 7), rabies (e.g., GenBank Accession No. M34678), yellow fever, Japanese encephalitis (e.g., GenBank Accession No. E07883), dengue (e.g., GenBank Accession No. M24444), hantavirus, and human immunodeficiency virus (e.g., GenBank Accession No. U18552).

Suitable bacterial and parasitic antigens include those derived from known causative agents responsible for diseases including, but not limited to, diphtheria, pertussis (e.g., GenBank Accession No. M35274), tetanus (e.g., GenBank Accession No. M64353), tuberculosis, bacterial and fungal pneumonias (e.g., *Haemophilus* influenzae, *Pneumocystis carinii*, etc.), cholera, typhoid, plague, shigellosis, salmonellosis (e.g., GenBank Accession No. L03833), Legionnaire's Disease, Lyme disease (e.g., GenBank Accession No. U59487), malaria (e.g., GenBank Accession No. X53832), hookworm, onchocerciasis (e.g., GenBank Accession No. M27807), schistosomiasis (e.g., GenBank Accession No. L08198), trypanosomiasis, leshmaniasis, giardiasis (e.g., GenBank Accession No. M33641), amoebiasis, filariasis (e.g., GenBank Accession No. J03266), borreliosis, and trichinosis.

Polypeptides and peptide epitopes associated with microbial pathogens are known in the art and include, but are not limited to, antigens associated with human immunodeficiency virus (HIV), e.g., HIV gp120, or an antigenic fragment thereof; cytomegalovirus antigens; *Mycobacterium* antigens (e.g., *Mycobacterium avium*, *Mycobacterium tuberculosis*, and the like); *Pneumocystic carinii* (PCP) antigens; malarial antigens, including, but not limited to, antigens associated with *Plasmodium falciparum* or any other malarial species, such as 41-3, AMA-1, CSP, PFEMP-1, GBP-130, MSP-1, PFS-16, SERP, etc.; fungal antigens; yeast antigens (e.g., an antigen of a *Candida* spp.); toxoplasma antigens, including, but not limited to, antigens associated with *Toxoplasma gondii*, *Toxoplasma encephalitis*, or any other *Toxoplasma* species; Epstein-Barr virus (EBV) antigens; and the like.

Pathogen-associated antigens are well known in the art; and many have been synthesized in the laboratory. See, e.g., U.S. Pat. No. 6,322,789, for a discussion of hepatitis B virus epitopes; U.S. Pat. No. 6,723,695 for a discussion of Epstein-Barr virus epitopes; etc.

Additional antigens of interest include antigens to which a person may have been exposed, including, but not limited to, *Mycobacterium bovis* (Bacille Calmette-Guerin); poxvirus antigens; and the like.

Further antigens of interest include antigens associated with or produced by weapons-grade pathogenic organisms ("biological warfare agents" or "bioterror agents"). Biological warfare agents include spore forming bacteria (e.g., anthrax), vegetative bacteria (e.g., plague, cholera), viruses (e.g., smallpox, yellow fever), and bacterial toxins (e.g., botulinum toxin, ricin).

Bacterial biological warfare agents include, but are not limited to, *Yersinia pestis, Bacillus anthracis, Vibro cholerae*, and the like. Bacterial biological warfare agents include bacteria that are developed, and/or produced, and/or used specifically for the purpose of inflicting disease and/or death upon a human population (where "human population" includes military personnel and civilian populations). Bacterial biological warfare agents include naturally-occurring (e.g., wild-type) bacteria as listed above; a naturally-occurring variant of any of the above-listed bacteria; and variants generated in the laboratory, including variants generated by selection, variants generated by chemical modification, and genetically modified variants (e.g., bacteria modified in a laboratory by recombinant DNA methods). Recombinant or synthetic viral biological warfare agents include variants of the above-listed bacteria that have increased virulence compared to a wild-type bacterium, and/or increased stability (e.g., storage stability at extreme high temperatures, and the like) compared to a wild-type bacterium, etc.

The term "viral biological warfare agent," as used herein, refers generally to any viral agent that is developed, and/or produced, and/or used specifically for the purpose of inflicting disease and/or death upon a human population (where "human population" includes military personnel and civilian populations). Such viral agents include, but are not limited to, Nipah virus; Hantavirus; alphaviruses that cause encephalitis, including, but not limited to, Venezuelan equine encephalitis virus, eastern equine encephalitis virus, and western equine encephalitis virus; and viruses that cause hemorrhagic fevers, including, but not limited to, filoviruses (e.g., Marburg virus, Ebola virus, and the like), Crimean Congo hemorrhagic fever virus, dengue virus, and arenaviruses (e.g., Lassa virus, Machupo virus, and the like). Also included in the term "viral biological warfare agents" are any subtype, serotype, isolate, or strain of any of the foregoing viruses.

The term "viral biological warfare agents" further includes naturally-occurring (e.g., wild-type) viruses as listed above; a naturally-occurring variant of any of the above-listed viruses; and variants generated in the laboratory, including variants generated by selection, variants generated by chemical modification, and genetically modified variants (e.g., virus modified in a laboratory by recombinant DNA methods). Variant viruses generated in the laboratory are referred to herein as "recombinant viruses" or "synthetic viruses." Recombinant or synthetic viral biological warfare agents include variants of the above-listed viruses that have increased virulence compared to a wild-type virus, and/or increased stability (e.g., storage stability at extreme high temperatures, and the like) compared to a wild-type virus, etc.

Exogenous RNA Encoding Therapeutic Proteins

In some embodiments, the exogenous RNA is one that includes a coding region that encodes a protein that a eukaryotic host cell or eukaryotic host is in need of. For example, in some embodiments, the encoded polypeptide is one that the eukaryotic host cell does not produce (e.g., due to a mutation in the eukaryotic host cells). In other embodiments, the encoded polypeptide is one that the eukaryotic host cell produces, but only at low levels, such that increasing the level of the protein using a subject bacterial delivery system increases the level of the protein. In other embodiments, the encoded protein is a functional variant of an endogenous protein that the eukaryotic host cell produces, e.g., where the eukaryotic host cell produces a non-functional protein, and the exogenous RNA comprises a nucleotide sequence that encodes a functional variant of the endogenous protein.

The exogenous RNA comprises a nucleotide sequence that encodes an exogenous polypeptide. Exogenous polypeptides include, but are not limited to, antibiotics, insecticides, fungicides, anti-viral agents, anti-protozoan agents, enzymes, anti-cancer agents (e.g. cyclin dependent kinase (CDK) inhibitors such as P16, P21 or P27), antibodies, anti-inflammatory peptides, cytokines, chemokines, transcription factors, antigenic peptides, etc.

Suitable exogenous polypeptides include, but are not limited to: an interferon (e.g., IFN-$\gamma$, IFN-$\alpha$, IFN-$\beta$, IFN-$\omega$; IFN-$\tau$); an insulin; an erythropoietin; an antibody, including an antigen-binding fragment of a monoclonal antibody; a blood factor, e.g., tissue plasminogen activator, a clotting factor, hemoglobin, and the like; a colony stimulating factor, e.g., granulocyte colony stimulating factor (G-CSF), granulocyte-monocyte colony stimulating factor, macrophage colony stimulating factor, megakaryocyte colony stimulating factor; and the like); a growth hormone, e.g., a somatotropin, and the like; an interleukin (e.g., IL-1; IL-2, IL-3, IL-4, IL-5, IL-6, IL-7, IL-8, IL-9; etc.); a growth factor, e.g., PDGF, bFGF, stem cell factor, and the like; keratinocyte growth factor; an acidic fibroblast growth factor, a stem cell factor, a basic fibroblast growth factor, a hepatocyte growth factor; and the like); a soluble receptor, e.g., a TNF-$\alpha$-binding soluble receptor a soluble VEGF receptor; a soluble interleukin receptor; a soluble $\gamma$/$\delta$ T cell receptor; and the like; an enzyme, e.g., $\alpha$-glucosidase; $\beta$-glucocerebrosidase, and the like; an enzyme activator, e.g., tissue plasminogen activator; a chemokine (e.g., IP-10; Mig; Gro$\alpha$/IL-8, RANTES; MIP-1$\alpha$; MIP-1$\beta$; MCP-1; PF-4; and the like); an angiogenic agent (e.g., vascular endothelial growth factor (VEGF); an anti-angiogenic agent (e.g., a soluble VEGF receptor); a protein vaccine; a neuroactive peptide such as bradykinin, cholecystokinin, gastin, secretin, oxytocin, gonadotropin-releasing hormone, beta-endorphin, enkephalin, substance P, somatostatin, prolactin, galanin, growth hormone-releasing hormone, bombesin, warfarin, dynorphin, neurotensin, motilin, thyrotropin, neuropeptide Y, luteinizing hormone, calcitonin, insulin, glucagon, vasopressin, angiotensin II, thyrotropin-releasing hormone, vasoactive intestinal peptide, a sleep peptide, etc.; other proteins such as a thrombolytic agent, an atrial natriuretic peptide, bone morphogenic protein, thrombopoietin, relaxin, glial fibrillary acidic protein, follicle stimulating hormone, a human alpha-1 antitrypsin, a leukemia inhibitory factor, a transforming growth factor, a tissue factor, an insulin-like growth factor, a luteinizing hormone, a follicle stimulating hormone, a macrophage activating factor, tumor necrosis factor, a neutrophil chemotactic factor, a nerve growth factor, a tissue inhibitor of metalloproteinases; a vasoactive intestinal peptide, angiogenin, angiotropin, fibrin; hirudin; a leukemia inhibitory factor; an IL-1 receptor antagonist; and the like. Also suitable are fusion proteins comprising all or a portion of any of the foregoing proteins.

Exogenous RNA that Controls Gene Expression

In some embodiments, an exogenous RNA is one that controls expression of a target gene in the mammalian host cell, e.g., that inhibit translation of target mRNA in the mammalian host cell. The target gene in the mammalian host cell is referred to herein as "the target gene," or "the target mRNA," and will in various embodiments be a gene that is endogenous to the mammalian host cell, a viral gene that is present in the mammalian host cell, a gene of a pathogen that is present in the mammalian host cell, or a transgene present in the mammalian host cell.

In many embodiments, the exogenous RNA is a double-stranded RNA (dsRNA). In these embodiments, the exogenous dsRNA comprises a nucleotide sequence that hybridizes under stringent conditions to a nucleotide sequence of the target gene. In some embodiments, the bacterium produces long ds exogenous RNA, and an RNAse III or RNAse III-like enzyme, such as Dicer, such that the long ds exogenous RNA is processed into siRNA of 20-25 base pairs (bp) in length. The dsRNA comprises a first nucleotide sequence that hybridizes under stringent conditions, including a wash step of 0.2×SSC (where 1×SSC is 0.15 M NaCl and 15 mM citrate buffer) at 65° C., to a nucleotide sequence of at least one mammalian gene and a second nucleotide sequence which is complementary to the first nucleotide sequence.

As used herein, the term "stringent hybridization conditions" are those normally used by one of skill in the art to establish at least an 80%, or at least a 90% sequence identity between complementary pieces of DNA or DNA and RNA. Nucleic acid hybridization conditions routinely used are set out in readily available procedure texts (e.g., Current Protocol in Molecular Biology, Vol. 1, Chap. 2.10, John Wiley & Sons, Publishers (1994); Sambrook et al., Molecular Cloning, Cold Spring Harbor (1989)). Stringent hybridization conditions will in some embodiments comprise: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5× Denhardt's solution, 0.05% sodium pyrophosphate and 100 μg/ml herring sperm DNA; hybridization for 18-20 hours at 65° C. in a solution containing 6×SSC, 1× Denhardt's solution, 100 μg/ml yeast tRNA and 0.05% sodium pyrophosphate; and washing of filters at 65° C. for 1 hour in a solution containing 0.2×SSC and 0.1% SDS (sodium dodecyl sulfate).

Suitable exogenous RNA that encode control target gene expression include non-translated RNAs, such as an antisense RNA, a ribozyme, an RNAi and an siRNA. Interfering RNA (RNAi) fragments, particularly double-stranded (ds) RNAi, can be used to inhibit gene expression. One approach well known in the art for inhibiting gene expression is short interfering RNA (siRNA) mediated gene silencing, where the level of expression product of a target gene is reduced by specific double stranded siRNA nucleotide sequences that are complementary to at least a 19-25 nucleotide long segment (e.g., a 20-21 nucleotide sequence) of the target gene transcript, including the 5' untranslated (UT) region, the ORF, or the 3' UT region. In some embodiments, short interfering RNAs are about 19-25 nt in length. See, e.g., PCT applications WO0/44895, WO99/32619, WO01/75164, WO01/92513, WO01/29058, WO01/89304, WO02/16620, and WO02/29858; U.S. Patent Publication No. 20040023390; and U.S. Patent Publication No. 20040086884 for descriptions of siRNA technology. The siRNA can be encoded by a nucleic acid, and the nucleic acid can also include a promoter operably linked to the siRNA-encoding nucleic acid. The nucleic acid sequence can also include a polyadenylation signal. In some embodiments, the polyadenylation signal is a synthetic minimal polyadelylation signal.

In some embodiments, the first nucleotide sequence of a double-stranded RNA is about 20 nucleotides, about 21 nucleotides, about 22 nucleotides, from about 22 nucleotides to about 25 nucleotides, from about 50 nucleotides to about 100 nucleotides, from about 100 nucleotides to about 200 nucleotides, from about 200 nucleotides to about 300 nucleotides, from about 300 nucleotides to about 400 nucleotides, from about 400 nucleotides to about 500 nucleotides, or from about 500 nucleotides to about 800 nucleotides in length.

In some embodiments, the first nucleotide sequence of the dsRNA is identical to at least one target gene. In another embodiment, the first nucleotide sequence of the dsRNA is identical to one target gene. In yet another embodiment, the first nucleotide sequence of the dsRNA hybridizes under stringent conditions to at least one target gene.

"Inhibition of gene expression" refers to the absence (or detectable decrease) in the level of protein and/or mRNA product from a target gene, where a dsRNA that controls expression of a target gene reduces translation of the target mRNA by at least about 10%, at least about 20%, at least about 30%, at least about 50%, at least about 75%, or more, compared to the level of translation of the target mRNA in the absence of the dsRNA.

In many embodiments, inhibition is specific to the target gene. "Specificity" as used herein refers to the ability to inhibit the target gene without manifest effects on other genes of the cell. The consequences of inhibition can be confirmed by examination of the outward properties of the cell or organism or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS). For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin.

Target genes (an endogenous gene in the mammalian host cell, a gene of a pathogen present in the mammalian host cell, etc.) include any gene encoding a target gene product (RNA or protein) that is deleterious (e.g., pathological); a target gene product that is malfunctioning; and a target gene product. Target gene products include, but are not limited to, huntingtin; hepatitis C virus; human immunodeficiency virus; amyloid precursor protein; tau; a protein that includes a polyglutamine repeat; a herpes virus (e.g., *varicella zoster*); any pathological virus; a gene of any pathogen, e.g., a *Mycobacterium*; and the like. Further suitable target genes include developmental genes (e.g., adhesion molecules, cyclin kinase inhibitors, Writ family members, Pax family members, Winged helix family members, Hox family members, cytokines/lymphokines and their receptors, growth/differentiation factors and their receptors, neurotransmitters and their receptors); oncogenes (e.g., ABLI, BCLI, BCL2, BCL6, CBFA2, CBL, CSFIR, ERBA, ERBB, EBRB2, ETSI, ETS1, ETV6, FGR, FOS, FYN, HCR, HRAS, JUN, KRAS, LCK, LYN, MDM2, MLL, MYB, MYC, MYCL1, MYCN, NRAS, PIM 1, PML, RET, SRC, TAL1, TCL3, and YES); tumor suppressor genes (e.g., APC, BRCA 1, BRCA2, MADH4, MCC, NF 1, NF2, RB 1, TP53, and WT1); and enzymes (e.g., ACC synthases and oxidases, ACP desaturases and hydroxylases, ADP-glucose pyrophorylases, ATPases, alcohol dehydrogenases, amylases, amyloglucosidases, catalases, cellulases, chalcone synthases, chitinases, cyclooxygenases, decarboxylases, dextrinases, DNA and RNA polymerases, galactosidases, glucanases, glucose oxidases, granule-bound starch synthases, GTPases, helicases, hemicellulases, integrases, inulinases, invertases, isomerases, kinases, lactases, lipases, lipoxygenases, lysozymes, nopaline synthases, octopine synthases, pectinesterases, peroxidases, phosphatases, phospholipases, phosphorylases, phytases, plant growth regulator synthases, polygalacturonases, proteinases and peptidases, pullanases, recombinases, reverse transcriptases, RUBISCOs, topoisomerases, and xylanases.

As such, a subject modified bacterium that synthesizes an exogenous siRNA is useful for treating a variety of disorders and conditions, including, but not limited to, neurodegenerative diseases, e.g., a trinucleotide-repeat disease, such as a disease associated with polyglutamine repeats, e.g., Huntington's disease, spinocerebellar ataxia, spinal and bulbar muscular atrophy (SBMA), dentatorubropallidoluysian atrophy (DRPLA), etc.; an acquired pathology (e.g., a disease or syndrome manifested by an abnormal physiological, biochemical, cellular, structural, or molecular biological state) such as a viral infection, e.g., hepatitis that occurs or may occur as a result of an HCV infection, acquired immunodeficiency syndrome, which occurs as a result of an HIV infection; and the like.

Promoters

An exogenous nucleic acid encoding an exogenous RNA is operably linked to a promoter. Suitable promoters include any promoter that is functional in the genetically modified bacterium. Suitable promoters include, but are not limited to a bacteriophage T7 RNA polymerase promoter; a T7/lac promoter; a trc promoter; a tac promoter; a trp promoter; a lac operon promoter; a hybrid promoter, e.g., a lac/tac hybrid promoter, a tac/trc hybrid promoter, a trp/lac promoter, and the like; a bad/ara promoter; in vivo regulated promoters, such as an ssaG promoter or a related promoter (see, e.g., U.S. Patent Publication No. 20040131637), a pagC promoter (Pulkkinen and Miller, J. Bacteriol., 1991: 173(1): 86-93; Alpuche-Aranda et al., PNAS, 1992; 89(21): 10079-83), a nirB promoter (Harborne et al. (1992) Mol. Micro. 6:2805-2813), and the like (see, e.g., Dunstan et al. (1999) Infect. Immun. 67:5133-5141; McKelvie et al. (2004) Vaccine 22:3243-3255; and Chatfield et al. (1992) Biotechnol. 10:888-892); a stationary phase promoter, e.g., a dps promoter, an spv promoter, and the like; a promoter derived from the pathogenicity island SPI-2 (see, e.g., WO96/17951); an actA promoter (see, e.g., Shetron-Rama et al. (2002) Infect. Immun. 70:1087-1096); an rpsM promoter (see, e.g., Valdivia and Falkow (1996). Mol. Microbiol. 22:367-378); a tet promoter (see, e.g., Hillen, W. and Wissmann, A. (1989) In Saenger, W. and Heinemann, U. (eds), Topics in Molecular and Structural Biology, Protein-Nucleic Acid Interaction. Macmillan, London, UK, Vol. 10, pp. 143-162); an SP6 promoter (see, e.g., Melton et al. (1984) Nuc. Acids Res. 12:7035-7056); and the like.

Compositions Comprising a Subject Bacterium

The present invention further provides compositions, including pharmaceutical compositions, and immunogenic compositions, comprising a subject bacterium. The present invention further provides compositions including pharmaceutical compositions and immunogenic compositions, comprising a subject bacterial population. Typically, a subject bacterium is cultured in vitro under conditions and for a suitable period of time such that exogenous RNA is synthesized by the bacterium. In some embodiments, the bacterium/bacteria is then formulated in a composition suitable for delivery to a mammalian subject.

Compositions comprising a subject bacterium may include a buffer, which is selected according to the desired use of the subject bacterium, and may also include other substances appropriate to the intended use. Those skilled in the art can readily select an appropriate buffer, a wide variety of which are known in the art, suitable for an intended use. In some instances, the composition can comprise a pharmaceutically acceptable excipient, a variety of which are known in the art and need not be discussed in detail herein. Pharmaceutically acceptable excipients have been amply described in a variety of publications, including, for example, "Remington: The Science and Practice of Pharmacy", 19th Ed. (1995) Mack Publishing Co; A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7th ed., Lippincott, Williams, & Wilkins; and Handbook of Pharmaceutical Excipients (2000) A. H. Kibbe et al., eds., 3rd ed. Amer. Pharmaceutical Assoc.

Pharmaceutical compositions can be prepared in various forms, such as granules, tablets, pills, suppositories, capsules, suspensions, sprays, suppositories, transdermal applications (e.g., patches, etc.), salves, lotions and the like. Pharmaceutical grade organic or inorganic carriers and/or diluents suitable for oral and topical use can be used to make up compositions containing the therapeutically active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents. In some embodiments, a subject bacterium is processed for storage, e.g., lyophilized. In some embodiments, a subject bacterium is cultured in vitro under conditions such that exogenous RNA is synthesized; after which the bacteria are lyophilized.

When used as an immunogenic composition, a subject bacterium can be formulated in a variety of ways. In general, an immunogenic composition of the invention is formulated according to methods well known in the art using suitable pharmaceutical carrier(s) and/or vehicle(s). A suitable vehicle is sterile saline. Other aqueous and non-aqueous isotonic sterile injection solutions and aqueous and non-aqueous sterile suspensions known to be pharmaceutically acceptable carriers and well known to those of skill in the art may be employed for this purpose.

Optionally, an immunogenic composition of the invention may be formulated to contain other components, including, e.g., adjuvants, stabilizers, pH adjusters, preservatives and the like. Such components are well known to those of skill in the vaccine art. Adjuvants include, but are not limited to, aluminum salt adjuvants (Nicklas (1992) Res. Immunol. 143: 489-493); saponin adjuvants; Ribi's adjuvants (Ribi ImmunoChem Research Inc., Hamilton, Mont.); Montanide ISA adjuvants (Seppic, Paris, France); Hunter's TiterMax adjuvants (CytRx Corp., Norcross, Ga.); Gerbu adjuvants (Gerbu Biotechnik GmbH, Gaiberg, Germany); and nitrocellulose (Nilsson and Larsson (1992) Res. Immunol. 143:553-557). In addition, other components that may modulate an immune response may be included in the formulation, including, but not limited to, cytokines, such as interleukins; colony-stimulating factors (e.g., GM-CSF, CSF, and the like); and tumor necrosis factor.

In some embodiments, a subject composition (including an immunogenic composition) comprises a plurality of bacteria, e.g., from about $10^2$ bacteria to about $10^{12}$ bacteria, e.g., from about $10^2$ bacteria to about $10^4$ bacteria, from about $10^4$ bacteria to about $10^6$ bacteria, from about $10^6$ bacteria to about $10^8$ bacteria, from about $10^8$ bacteria to about $10^{10}$ bacteria, or from about $10^{10}$ bacteria to about $10^{12}$ bacteria. In some embodiments, a subject composition comprises a library (or population or mixture or cocktail) of bacteria, comprising bacteria that produce different exogenous RNAs. For example, the population of bacteria comprises at least two member bacteria, each of the member bacteria synthesizes a different exogenous RNA, each of which encodes a different exogenous polypeptide.

For example, in some embodiments, the population of bacteria includes at least two members, each of which synthesizes a different exogenous RNA, each of which exogenous RNAs encode a different human immunodeficiency virus (HIV) polypeptide or fragment thereof, which polypeptides or fragments are antigenic. In some of these embodiments, the HIV is HIV type-1. In some embodiments, the at least two different antigenic polypeptides, or fragments thereof, are selected from the group consisting of gag, env, pol and nef polypeptides from HIV. In some of these embodiments, the population comprises nucleotide sequences encoding overlapping fragments of the gag, env, pol and nef polypeptides and each fragment has a length from about four amino acids to about 400 amino acids, from about four amino acids to about 100 amino acids, or from about 100 amino acids to about 250 amino acids.

Methods of Use of a Subject Bacterium

The present invention further provides methods of delivering a gene product (an RNA and/or a polypeptide) to an individual in need thereof. The methods generally involve introducing a subject bacterium, or a subject bacterial population, into an individual in need of the gene product. The instant invention provides methods of delivering an RNA to a mammalian host cell in vitro, ex vivo, or in vivo. The methods generally involve infecting a mammalian host cell in vitro, ex vivo, or in vivo with a subject bacterium, or a subject bacterial population, which comprises exogenous RNA. In some embodiments, the RNA corresponds to a replication competent viral genome that can amplify its own RNA and/or produce progeny virus and propagate to other cells.

Delivering a Polypeptide

The instant invention provides methods of delivering an exogenous polypeptide to a mammalian host in vivo. The method generally involves administering to a mammalian host a subject bacterium (or a composition comprising a subject bacterium), or a subject bacterial population, wherein the subject bacterium enters a eukaryotic host cell (e.g., an APC, an intestinal epithelial cell, a dendritic cell, etc.), and releases the exogenous RNA, produced by the bacterium in vitro (and/or after entry of the bacterium into the eukaryotic host cell), into the cytoplasm of host cell, where the exogenous RNA is translated and the exogenous polypeptide is synthesized in the host cell. In some embodiments, the exogenous polypeptide will remain within the eukaryotic host cell. In other embodiments, the exogenous polypeptide will be secreted from the eukaryotic host cell (e.g., into the bloodstream of the host, into the interstitial fluids in the host, etc.). In other embodiments, the exogenous polypeptide will be processed within the eukaryotic host cell and will in some embodiments be displayed on the surface of the eukaryotic host cell (e.g., displayed with a major histocompatibility complex protein on the surface of the host cell). In other embodiments, the exogenous polypeptide will be secreted from the eukaryotic host cell and will be taken up by another cell in the host organism. In other embodiments, the exogenous polypeptide will be secreted from the eukaryotic host cell and will act on another cell in the eukaryotic host (e.g., will bind to a cell surface receptor on another host cell, etc.).

Inhibiting Growth of a Cancer Cell in a Host

The instant invention provides methods of inhibiting growth of a cancer cell, and methods of inhibiting tumor growth, in a subject. The methods generally involve administering to an individual having a cancerous cell a subject bacterium or a composition comprising a subject bacterium or a subject bacterial population. In some embodiments, the bacterium comprises RNA comprising a nucleotide sequence encoding a polypeptide that inhibits tumor growth. In other embodiments, the bacterium comprises an RNA that inhibits expression of a target gene in a cancer cell, such that growth of the cancer cell is inhibited.

In some embodiments, the subject bacterium is one that preferentially infects tumor cells. For example, a bacterium that preferentially infects tumor cells accumulates in a tumor cell at a ration of at least about 100:1, at least about 200:1, at least about 300:1, at least about 400:1, at least about 500:1, at least about 700:1, or at least about 1000:1, compared to non-cancerous cells.

A subject bacterium that is suitable for inhibiting growth of a cancer cell is a bacterium that comprises nucleic acid encoding an RNA that comprises a nucleotide sequence that encodes a polypeptide that directly or indirectly inhibits growth of a cancer cell. Suitable polypeptides include, but are not limited to, cytostatic agents that block the cell cycle and arrest cell proliferation; polypeptides that stimulate a cytostatic or cytotoxic response; a cytosine deaminase (e.g., E. coli cytosine deaminase); a nitroreductase (e.g., E. coli nitroreductase); a polypeptide that inhibits angiogenesis; a cytokine; a colicin (e.g., colicin E3); polypeptides that convert a prodrug into a cytotoxic agent (e.g., thymidine kinase); polypeptides that induce apoptosis in an endothelial cell in the endothelium of a vascularized tumor; polypeptides that induce apoptosis in a tumor cell; and the like. Suitable cytokines include, but are not limited to, TNF-α, IL-2, IL-4, TGF-γ, IFN-α, and the like. Suitable polypeptides that inhibit angiogenesis include, but are not limited to, endostatin, angiostatin, vasculostatin, an anti-angiogenic angiopoietin, angioarrestin (see, e.g., Dhanabal et al. (2002) *Cancer Res.* 62:3834-3841), a tissue inhibitor of metalloproteinase, platelet factor-4 (PF4), a soluble vascular endothelial growth factor receptor (see, e.g., U.S. Patent Publication No. 20030181377), and the like. See, e.g., U.S. Pat. No. 6,783,760.

Cytostatic agents that block the cell cycle and arrest cell proliferation include, but are not limited to cyclin-dependent kinase inhibitors (CDKIs) such as p16, p21, and p27; p53, p53175P, p57 (Kip2), p15 (INK4b), p18(INK4c), p19(Arf), p73, GADD45, APC1, p73RB1, WT1, NF1, VHL, and the like. See, e.g., Koga et al. (2001) *Hepatology* 33:1087-1097; Xiong et al. (1993) *Nature* 366:701-704; Grana and Reddy (1995) *Oncogene* 11:211-219; Huang et al. (2001) *Cancer Res.* 61:3373-3381).

Polypeptides that stimulate a cytostatic or cytotoxic response include, but are not limited to, thymidine kinase, interferons (e.g., alpha-interferon, beta-interferon, gamma-interferon), interferon inducers, thymic factors (e.g., thymosin-alpha-1), and variants thereof. Further, polypeptides that stimulate an immune response (e.g., a cytotoxic T lymphocyte response to a cancer cell) are also suitable. Polypeptides that stimulate an immune response include, but are not limited to, lymphokines (e.g., IL-1, IL-2, IL-3, IL-4), colony stimulating factors (e.g., G-CSF, GM-CSF, and M-CSF), and variants thereof.

A subject bacterium that is suitable for inhibiting growth of a cancer cell is a bacterium that comprises nucleic acid encoding an RNA that controls expression of a target gene or nucleic acid, and that directly or indirectly inhibits growth of a cancer cell. Suitable target genes include genes encoding gene products involved in cell maintenance or maintenance of the cancerous cell phenotype. Suitable target genes include, but are not limited to, cdk2, cdk8, cdk2, cdc25A, cyclindD1, cyclinE, cyclinA and cdk4. Suitable target genes also include oncogenes that inhibit apoptosis, including, but not limited to, bcr-ab1, bcl-2, and family members including Bcl-x1, Mcl-1, Bak, A1, A20. Suitable target genes include tumor suppressors, e.g., p53, Retinoblastoma gene (Rb), Wilm's tumor (WT1), bax alpha, interleukin-1b-converting enzyme and family, MEN-1 gene, neurofibromatosis, type 1 (NF1), cdk inhibitor p16, colorectal cancer gene (DCC), familial adenomatosis polyposis gene (FAP), multiple tumor suppressor gene (MTS-1), BRCA1, and BRCA2; as well as oncogenic forms of c-fos, c-jun, Kr-ras, and Her2/neu.

In some embodiments, an "effective amounts" of a subject bacterium, an exogenous polypeptide encoded by RNA delivered by the bacterium, or an RNA delivered by the bacterium, is an amount that that alone or in combination with other therapy for cancer is sufficient to reduce tumor load or reduce tumor progression by at least about 5%, at least about 10%, at least about 20%, at least about 25%, at least about 50%, at least about 75%, at least about 85%, or at least about 90%, up to total eradication of the tumor, or total inhibition of tumor progression, when compared to a suitable control. In an experimental animal system, a suitable control may be a genetically identical animal not treated with the subject bacterium. In non-experimental systems, a suitable control may be the tumor load present before administering the subject bacterium. Other suitable controls may be a placebo control.

Whether a tumor load has been decreased can be determined using any known method, including, but not limited to, measuring solid tumor mass; counting the number of tumor cells using cytological assays; fluorescence-activated cell sorting (e.g., using antibody specific for a tumor-associated antigen) to determine the number of cells bearing a given tumor antigen; computed tomography scanning, magnetic resonance imaging, and/or x-ray imaging of the tumor to estimate and/or monitor tumor size; measuring the amount of tumor-associated antigen in a biological sample, e.g., blood; and the like.

The methods are effective to reduce the growth rate of a tumor by at least about 5%, at least about 10%, at least about 20%, at least about 25%, at least about 50%, at least about 75%, at least about 85%, or at least about 90%, up to total inhibition of growth of the tumor, when compared to a suitable control. Thus, in these embodiments, an "effective amount" of a subject bacterium, an exogenous polypeptide encoded by RNA delivered by the bacterium, or an RNA delivered by the bacterium, is an amount that, alone or in combination with other therapy for cancer, is sufficient to reduce tumor growth rate by at least about 5%, at least about 10%, at least about 20%, at least about 25%, at least about 50%, at least about 75%, at least about 85%, or at least about 90%, up to total inhibition of tumor growth, when compared to a suitable control. In an experimental animal system, a suitable control may be a genetically identical animal not treated with the subject bacterium. In non-experimental systems, a suitable control may be the tumor growth rate existing before administering the subject bacterium. Other suitable controls may be a placebo control.

Whether growth of a tumor is inhibited can be determined using any known method, including, but not limited to, a proliferation assay; a 3H-thymidine uptake assay; and the like.

The methods are useful for treating a wide variety of cancers, including carcinomas, sarcomas, leukemias, and lymphomas.

Carcinomas that can be treated using a subject method include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelieal carcinoma, and nasopharyngeal carcinoma, etc.

Sarcomas that can be treated using a subject method include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Other solid tumors that can be treated using a subject method include, but are not limited to, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Leukemias that can be treated using a subject method include, but are not limited to, a) chronic myeloproliferative syndromes (neoplastic disorders of multipotential hematopoietic stem cells); b) acute myelogenous leukemias (neoplastic transformation of a multipotential hematopoietic stem cell or a hematopoietic cell of restricted lineage potential; c) chronic lymphocytic leukemias (CLL; clonal proliferation of immunologically immature and functionally incompetent small lymphocytes), including B-cell CLL, T-cell CLL, prolymphocytic leukemia, and hairy cell leukemia; and d) acute lymphoblastic leukemias (characterized by accumulation of lymphoblasts). Lymphomas that can be treated using a subject method include, but are not limited to, B-cell lymphomas (e.g., Burkitt's lymphoma); Hodgkin's lymphoma; and the like.

A subject bacterium that is suitable for the treatment of cancer can be used as an adjuvant to a standard cancer therapy. Thus, the present invention provides methods of treating cancer in an individual having cancer, the methods involving administering a subject bacterium or bacterial population; and administering to the individual a standard cancer therapy. Standard cancer therapies include surgery (e.g., surgical removal of cancerous tissue), radiation therapy, bone marrow transplantation, chemotherapeutic treatment, biological response modifier treatment, and certain combinations of the foregoing.

Radiation therapy includes, but is not limited to, x-rays or gamma rays that are delivered from either an externally applied source such as a beam, or by implantation of small radioactive sources.

Chemotherapeutic agents are non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex®. Estrogens stimulate proliferation and differentiation, therefore compounds that bind to the estrogen receptor are used to block this activity. Corticosteroids may inhibit T cell proliferation.

Other chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

"Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., Taxotere™ docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

Biological response modifiers suitable for use in connection with the methods of the invention for treating cancer include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) IFN-α; (7) IFN-γ (8) colony-stimulating factors; and (9) inhibitors of angiogenesis.

Methods of Inducing an Immune Response

The instant invention further provides methods of inducing an immune response in a mammalian subject to an exogenous polypeptide. The method generally involves administering to a mammalian host a subject bacterium (or an immunogenic composition comprising a subject bacterium), or a subject bacterial population, wherein the subject bacterium comprising the exogenous RNA enters a host cell (e.g., an APC, an intestinal epithelial cell, etc.), and releases the exogenous RNA, produced by the bacterium in vitro, into the host cell, where the exogenous RNA is translated and the exogenous polypeptide is synthesized in the host cell, and wherein an immune response to the exogenous polypeptide is induced. In some embodiments, the immune response is a mucosal immune response.

Where the exogenous RNA encodes an antigenic protein, suitable antigenic proteins that can be delivered to an individual using a subject method include, but are not limited to, tumor-associated antigens, viral antigens, bacterial antigens, and protozoan antigens; and antigenic fragments thereof. In some embodiments, a cytotoxic T lymphocyte (CTL) response to the exogenous RNA-encoded antigenic protein will be induced in the mammalian host. In other embodiments, a humoral response to the exogenous RNA-encoded antigenic protein will be induced in the mammalian host, such that antibodies specific to the antigenic protein are generated. In many embodiments, a TH1 immune response to the exogenous RNA-encoded antigenic protein will be induced in the mammalian host. Whether an immune response to the antigenic protein has been generated is readily determined using well-established methods. For example, an enzyme-linked immunosorbent assay can be used to determine whether antibody to an antigenic protein has been generated. Methods of detecting antigen-specific CTL are well known in the art. For example, a detectably labeled target cell expressing the antigenic protein on its surface is used to assay for the presence of antigen-specific CTL in a blood sample.

In many embodiments, where an immune response to an exogenous polypeptide is induced, an immune response to a pathogenic organism that expresses one or more epitopes cross-reactive with the exogenous polypeptide is induced. Whether an immune response has been elicited to a pathogenic organism can be determined (quantitatively, e.g., by measuring a parameter, or qualitatively, e.g., by assessing the severity of a symptom, or by detecting the presence of a particular parameter) using known methods. Methods of measuring an immune response are well known in the art and include enzyme-linked immunosorbent assay (ELISA) for detecting and/or measuring antibody specific to a given pathogenic organism; and in vitro assays to measure a cellular immune response (e.g., a CTL assay using labeled, inactivated cells expressing the epitope on their cell surface with MHC Class I molecules). A biological sample obtained from the individual is used to test for the presence and/or quantity of antigen-specific antibody (e.g., serum IgG, mucosal IgA, etc.); and/or antigen-specific CTL. Suitable biological samples include, but are not limited to, serum; vaginal samples (e.g., fluids, cells); rectal samples (e.g., fluids, cells, etc.); blood; and the like. Whether a mucosal immune response is elicited can be determined using any known method, including, e.g., measuring secretory IgA, specific for an epitope(s) associated with the pathogenic organism, produced in a mucosal tissue.

Whether an immune response is effective to facilitate protection of the host against infection, or reduce symptoms associated with infection, by a pathogenic organism can be readily determined by those skilled in the art using standard assays, e.g., determining the number of pathogenic organisms in a host (e.g., measuring viral load, and the like); measuring a symptom caused by the presence of the pathogenic organism in the host (e.g., elevated body temperature; lower than normal $CD4^+$ T cell counts; weight loss; secondary infections; and the like).

In some embodiments, the exogenous polypeptide is a tumor-associated antigen (TAA). In these embodiments, a subject immunogenic composition is administered to an individual having, or suspected of having, a tumor. In some cases, the immunogenic composition is administered to an individual who does not have a tumor, but in whom protective immunity is desired. As is often the case, the immune system does not mount an immune response effective to inhibit or suppress tumor growth, or eliminate a tumor altogether. Tumor-associated antigens are often poorly immunogenic; perhaps due to an active and ongoing immunosuppression against them. Furthermore, cancer patients tend to be immunosuppressed, and only respond to certain T-dependent antigens. In these cases, introduction into the host of a subject immunogenic composition induces an immune response to a TAA corresponding to an antigen expressed on the tumor cell surface, and elicits an immune response to the tumor in the host.

Whether an immune response is elicited to a given tumor can be determined by methods standard in the art, including, but not limited to, assaying for the presence and/or amount of TAA-specific antibody in a biological sample obtained from the individual, e.g., by enzyme-linked immunosorbent assay (ELISA), radioimmunoassay (RIA), and the like; assaying for the presence and/or numbers of CTLs specific for a TAA; and the like. Examples of how to assay for the presence and/or numbers of antigen-specific CTLs are found in the Examples section herein below. Standard immunological protocols may be used, which can be found in a variety of texts, including, e.g., *Current Protocols in Immunology* (J. E. Coligan, A. M. Kruisbeek, D. H. Margulies, E. M. Shevach and W. Strober Eds. 1991).

Whether an immune response is effective in reducing the number of tumor cells in an individual can be determined by standard assays, including, but not limited to, measuring tumor cell mass, measuring numbers of tumor cells in an individual, and measuring tumor cell metastasis.

Delivering Viral RNA

The instant invention further provides methods for producing viral RNA or whole virus. The method generally involves introducing a subject bacterium into a host cell in vitro; and recovering the viral RNA produced, or the viral progeny produced. The methods are useful in vaccine production.

Method of Delivering an siRNA to a Host Cell

The instant invention further provides methods for delivering an siRNA to a eukaryotic host cell, the method generally involving introducing into the eukaryotic host cell a subject bacterium, or a subject bacterial population, that synthesizes an exogenous RNA, wherein the exogenous RNA is an siRNA. Such methods are useful for identifying the function of a gene in a eukaryotic host cell; and for modulating expression of a gene in a eukaryotic host cell.

Identifying the Function of a Gene in a Mammalian Host Cell

The instant invention further provides methods for identifying the function of a gene in a mammalian host cell, the method generally involving introducing into the cell a subject bacterium that comprises exogenous RNA, wherein the RNA is a siRNA; and detecting the effect, if any, of the siRNA on a host cell characteristic or a host cell function (e.g., an mRNA level of a gene; level of production of a protein encoded by a gene; any host cell function such as mitosis, interaction with other cells, etc.). Thus, the invention provides for functional genomics analyses, wherein a subject bacterium that produces a given siRNA is introduced into a mammalian host cell in vitro, and the effect, if any, of the siRNA on a host cell function or characteristic is detected.

Modulating Expression of a Target Gene

The present invention provides methods of modulating (e.g., inhibiting) expression of a target gene in a eukaryotic host cell. The methods generally involve administering to an individual in need thereof an effective amount of a subject bacterium, or a subject bacterial population, where the bacterium comprises an exogenous RNA that inhibits expression of a target gene in a eukaryotic host cell in the individual.

One approach well known in the art for inhibiting gene expression is short interfering RNA (siRNA) mediated gene silencing, where the level of expression product of a target gene is reduced by specific double stranded siRNA nucleotide sequences that are complementary to at least a 19-25 nucleotide long segment (e.g., a 20-21 nucleotide sequence) of the target gene transcript, including the 5' untranslated (UT) region, the ORF, or the 3' UT region. In some embodiments, short interfering RNAs are about 19-25 nt in length. See, e.g., PCT applications WO0/44895, WO99/32619, WO01/75164, WO01/92513, WO01/29058, WO01/89304, WO02/16620, and WO02/29858; and U.S. patent Publication No. 20040023390 for descriptions of siRNA technology. The siRNA can be encoded by a nucleic acid sequence, and the nucleic acid sequence can also include a promoter. The nucleic acid sequence can also include a polyadenylation signal. In some embodiments, the polyadenylation signal is a synthetic minimal polyadelylation signal.

Target genes include any gene encoding a target gene product (RNA or protein) that is deleterious (e.g., pathological); a target gene product that is malfunctioning; a target gene product. Target gene products include, but are not limited to, huntingtin; hepatitis C virus; human immunodeficiency virus; amyloid precursor protein; tau; a protein that includes a polyglutamine repeat; a herpes virus (e.g., *varicella zoster*); any pathological virus; and the like.

As such, a subject modified bacterium that synthesizes an exogenous RNA encoding an siRNA is useful for treating a variety of disorders and conditions, including, but not limited to, neurodegenerative diseases, e.g., a trinucleotide-repeat disease, such as a disease associated with polyglutamine repeats, e.g., Huntington's disease, spinocerebellar ataxia, spinal and bulbar muscular atrophy (SBMA), dentatorubro-pallidoluysian atrophy (DRPLA), etc.; an acquired pathology (e.g., a disease or syndrome manifested by an abnormal physiological, biochemical, cellular, structural, or molecular biological state) such as a viral infection, e.g., hepatitis that occurs or may occur as a result of an HCV infection, acquired immunodeficiency syndrome, which occurs as a result of an HIV infection; and the like.

Routes of Administration, Formulation, and Dosages

A subject bacterium (or a subject bacterial population) used in a subject method is administered to individuals in a formulation with a pharmaceutically acceptable excipient(s). Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7th ed., Lippincott, Williams, & Wilkins; and Handbook of Pharmaceutical Excipients (2000) A. H. Kibbe et al., eds., 3rd ed. Amer. Pharmaceutical Assoc.

In some embodiments, a subject composition comprises a subject bacterium. In other embodiments, a subject composition comprises a subject bacterial composition. In some embodiments, a subject composition is a pharmaceutical composition, e.g., the subject composition comprises a subject bacterium or a subject bacterial population; and a pharmaceutically acceptable excipient or carrier.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In the subject methods, a subject bacterium, a subject bacterial population, or a subject composition may be administered to the host using any convenient means capable of resulting in the desired therapeutic effect. Thus, the bacteria can be incorporated into a variety of formulations for therapeutic administration. More particularly, a subject bacterium can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. As such, administration of the agents can be achieved in various ways, including oral, buccal, rectal, parenteral, intraperitoneal, intradermal, subcutaneous, intramuscular, transdermal, intratracheal, etc., administration.

In some embodiments, a subject composition is administered orally. For oral preparations, the bacteria can be formulated alone or in combination with appropriate additives to make tablets, powders, liquid formulations, granules, or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of a subject bacterium calculated in an amount sufficient to produce the desired effect in association with a pharmaceutically acceptable diluent, carrier or vehicle.

The amount of a subject bacterium in each dose is selected as an amount which induces a desired effect (including, but not limited to, production of an encoded polypeptide, a therapeutic effect produced by an encoded polypeptide, production of a dsRNA, inhibition of target gene expression by an siRNA, and the like) without significant, adverse side effects. Such amount will vary depending upon various factors, e.g., which RNA is delivered to the host cell, which specific polypeptide is synthesized in the host cell or which dsRNA is delivered to the host cell, and a variety of host-dependent factors. In some embodiments, where the exogenous RNA encodes a protein, each dose of a subject bacterium will be sufficient to generate, upon infection of host cells, about 1-1000 µg of exogenous protein, generally from about 1-200 µg, normally from about 10-100 µg exogenous protein.

Alternatively, in some embodiments, an effective dose of a subject bacterial composition comprises subject bacteria in a range of from about $10^2$ to about $10^7$, from about $10^3$ to about $10^6$, or from about $10^4$ to about $10^5$ bacteria.

Administration will be selected as is appropriate for the eukaryotic host cells. Eukaryotic host cells may also be removed from the subject, contacted ex vivo with a subject bacterium, and the treated cells then replaced into the subject. Exemplary methods for in vivo administration are described in Shen et al., Proc Natl Acad Sci USA 1995, 92(9):3987-3991; Jensen et al, Immunol Rev 1997, 158: 147-157; Szalay et al., Proc Natl Acad Sci USA 1995, 92(26):12389-12392; Belyi et al, FEMS Immunol Med Microbiol 1996, 13(3): 211-213; Frankel et al., J. Immunol 1995, 155(10):4775-4782; Goossens et al., Int Immunol 1995, 7(5):797-805; Schafer et al., J. Immunol 1992, 149(1):53-59; and Linde et al., Vaccine 1991, 9(2):101-105.

Immunogenic Compositions

The invention provides immunogenic compositions comprising a live, attenuated, invasive bacterium of the invention. When they are used to induce or enhance an immune response, a subject bacterium is administered to an individual using known methods. A subject bacterium will generally be administered by the same routes by which conventional (presently-available) vaccines or other medications are administered and/or by routes which mimic the route by which infection by the pathogen of interest occurs. They can be administered in a composition which includes, in addition to the subject bacterium, a physiologically acceptable carrier. The composition may also include an immunostimulating agent or adjuvant, flavoring agent, or stabilizer.

Conventional and pharmaceutically acceptable routes of administration include intranasal, intramuscular, intratracheal, subcutaneous, intradermal, vaginal, intrapulmonary, intravenous, rectal, nasal, oral and various parenteral routes of administration. Routes of administration may be combined, if desired, or adjusted depending upon the disease. The immunogenic composition can be administered in a single dose or in multiple doses, and may encompass administration of booster doses, to elicit and/or maintain immunity.

The immunogenic compositions is administered in an "effective amount" that is, an amount of a subject bacterium that is effective in a selected route of administration to elicit or induce an immune response. An immune response is elicited to polypeptides encoded exogenous RNA produced by a subject bacterium, and therefore to antigens produced by a pathogenic organism. In some embodiments, the amount of a subject bacterium is effective to facilitate protection of the host against infection, and/or to reduce a symptom associated with infection, by a pathogenic organism. In some embodiments, an "effective amount" of an immunogenic composition is an amount of a subject bacterium that is effective in a route of administration to elicit an immune response effective to facilitate protection of the host against infection, and/or to reduce a symptom associated with infection, by a pathogenic organism.

The amount of a subject bacterium in each vaccine dose is selected as an amount which induces a desired immune response (including, but not limited to, an immunoprotective or other immunotherapeutic response) without significant, adverse side effects. Such amount will vary depending upon various factors, e.g., which specific immunogen is employed, whether or not the vaccine formulation comprises an adjuvant, and a variety of host-dependent factors. In some embodiments, each dose of immunogenic composition will be sufficient to generate, upon infection of host cells, about 1 µg to about 1000 µg of exogenous protein, e.g., from about 1-200 µg, or from about 10 µg to about 100 µg exogenous protein.

Alternatively, in some embodiments, an effective dose of a subject immunogenic composition comprises subject bacteria in a range of from about $10^2$ to about $10^7$, from about $10^3$ to about $10^6$, or from about $10^4$ to about $10^5$ bacteria. An optimal amount for a particular immunogenic composition can be ascertained by standard studies involving observation of antibody titers and other responses, e.g., CTL responses, in subjects. The levels of immunity provided by the immunogenic composition can be monitored to determine the need, if any, for boosters. For example, following an assessment of antibody titers in the serum, or $CD4^+$ T cell counts, CTL responses, and the like, optional booster immunizations may be desired. In some embodiments, the immune response to an exogenous protein encoded by an RNA delivered by a subject bacterium is enhanced by the use of adjuvant and or an immunostimulant.

In some embodiments, the compositions comprising a subject bacterium may be administered using conventional devices including but not limited to syringes, devices for intranasal administration of compositions, gene guns, and vaccine guns. Thus, one embodiment of the present invention is a device comprising a member which receives a subject bacterium or subject immunogenic composition in communication with a mechanism for delivering the composition to the subject. A subject immunogenic composition is in some embodiments formulated as a suppository, for vaginal or rectal delivery.

Subject Suitable for Treatment

Subjects suitable for treatment using a subject method include individuals having a disease or disorder that is amenable to treatment by delivering an RNA that controls expression of a target gene, or by delivering an RNA comprising a nucleotide sequence that encodes a polypeptide, as described above. For example, individuals who are suitable for treatment with a subject method for inhibiting growth of a cancer cell include individuals having a cancerous cell(s) or a tumor. Individuals who are suitable for treatment with a subject method for inducing an immune response include naive individuals (e.g., individuals who have never been exposed to a particular antigen or a particular pathogen); individuals who have not been exposed to a given pathogen, but who are at risk of exposure to the pathogen; and individuals who have been infected with a pathogen. Individuals who are suitable for treatment with a subject method for delivering a polypeptide include any individual who is in need of a given polypeptide, e.g., individuals who are hemophiliacs are suitable for treatment with a subject method of delivering a clotting factor, and the like. In many embodiments, treatment of humans is of interest.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s, second(s); min, minute(s); hr, hour(s); and the like.

Example 1

Preparation of a Bacterial Delivery System for Delivering RNA to a Eukaryotic Host Cell Two sets of recombinant live viruses derived from currently commercialized vaccine strains were developed—the Sabin strains of poliovirus, which have been rendered recombinant and allow the expression of foreign sequences correctly processed and cleaved from poliovirus proteins by synthetic protein cleavage sites, and the 17D strain of Yellow Fever virus, which has been engineered to express additional foreign sequences by the insertion of a second cistron. The cDNAs of poliovirus (PV) recombinants expressing the reporter protein GFP or the model antigen OVA and the cDNAs of Yellow Fever virus (YF) recombinants expressing the Luciferase protein or the model antigen p24 of HIV, have been placed under transcriptional control of the bacteriophage T7 RNA polymerase promoter and terminator. The resulting low copy plasmids are respectively, pPV-GFP, pPV-OVA and pYF-Luc, pYF-p24. HDVribozyme sequences were placed downstream of the genomes to facilitate production of RNA transcripts of appropriate length.

In vitro transcription of the PV and YF cDNAs and transfection of resulting transcripts into human cell lines confirms their capacity to produce progeny virus. Of key importance to the immunization strategy was the confirmation that such RNAs of the YF series remain infectious despite lacking a 5' cap, since the YF genome is normally a capped RNA. This finding permits one to continue to develop YF viruses as candidates for bacterial delivery purposes, as bacteria are unable to cap their RNAs. Next, *E. coli* that constitutively express T7 RNA polymerase were transformed with plasmids of the pPV and pYF series and total RNA was extracted to determine levels of RNA production corresponding to the PV and YF genomes. In all cases, apart from degraded bacterial mRNAs, the only detectable RNA transcripts corresponded to the viral genomes and demonstrated the superior transcriptional capacity of T7 polymerase with respect to bacterial RNA polymerases. Thus, despite the short half-life of bacterial RNAs, the vast majority of whole RNAs delivered to the host cell correspond to the recombinant viral RNA transcripts.

Methods: Attenuated *Salmonella typhimurium* strains, deleted of 3 genes (orgA, sifA and asd) and expressing the T7 RNA polymerase, were developed, to deliver the infectious RNA genomes of recombinant live viruses derived from vaccine strains (Sabin poliovirus-SIV and 17D Yellow Fever-HIVp24). The RNAs, produced within the bacteria by T7 polymerase were delivered to mucosal macrophages and epithelia. Deletion of orgA, sifA and asd genes ensures the “suicidal” release of RNAs into the cytoplasm of host cells, where they launch an infectious cycle expressing HIV antigens, as well as producing progeny virus to reinfect neighboring cells.

Results: To determine that RNA molecules produced in the bacteria were infectious, Yellow Fever virus and poliovirus cDNA plasmids were transformed into BL21 *E. coli*, which express T7 RNA polymerase. Total RNA was extracted and generation of progeny virus was confirmed by plaque assay. The ability of *Salmonella* carriers (wild type, orgA, sifA and asd mutants) to infect and deliver oligonucleotides to cell lines was studied with the aid of plasmids expressing GFP and Luciferase. The mutant strains orgA (apoptosis deficient), sifA (replication, vacuole localization deficient) and asd (cell wall constituent deficient) mutants were better able to deliver foreign sequences to host cells than was wild type.

Conclusions: These results provide proof of principle that a subject bacterial system can be used to deliver RNA to the cytoplasm of a host eukaryotic cell. For example, it has been shown that *Salmonella* expressing T7 RNA polymerase can transcribe and deliver the RNA genomes of recombinant live virus vaccines to the cytoplasm of macrophages and epithelial cells. These infectious RNAs launch and amplify the recombinant virus vaccine from within the infected cell.

Example 2

Characterization and Optimization of Bacterial Delivery of Recombinant RNA Transcripts to the Host Cell The sifA-DAP-T7+ *Salmonella* mutant is transformed with the pPV or pYF plasmids and grown in culture medium supplemented with DAP. Bacteria actively transcribing the recombinant RNAs are used to infect human cell lines, such as HeLa. At various times post-exposure to the *Salmonella* carriers, supernatants are titered to verify the production of recombinant poliovirus or Yellow Fever virus progeny, thereby confirming that the RNA transcripts were effectively delivered to the cytoplasm of the host cell by the bacteria. Alternatively, *Salmonella* infected HeLa cells are monitored for production of the reporter proteins (GFP or Luciferase). Production of foreign protein such as HIV p24, delivered by *Salmonella* transcribing the YF-p24 RNA, is confirmed by Western Blot analysis. Finally, the same procedure is applied to macrophage cell lines or primary macrophages isolated from both mice and humans.

Example 3

Immunogenicity Studies In Vivo

Following characterization in cell culture of this new approach to bacterial delivery, the efficiency with which the *Salmonella* mutants bearing the cDNA plasmids can deliver their transcribed RNAs to mucosal cells in vivo and effectively launch the recombinant virus infection permitting expression of foreign antigen is determined. Mice are inoculated via the oral route with *Salmonella* carrying the PV-OVA and YF-p24 constructs. Three weeks following immunization, levels of both serum and mucosal antibodies against the 24 antigen is determined. Furthermore, the induction of both systemic and local mucosal CTL responses directed against the OVA antigen is determined by ELISPOT and flow cytometry assays. Furthermore, a comparison is made between this system and 1) the use of *Salmonella* to deliver simple expression plasmids encoding the same antigens, rather than recombinant infectious RNAs and 2) immunization with the recombinant live viruses alone, without the aid of the bacterial carrier.

Example 4

Delivery of Polynucleotides by *Salmonella* Carriers

To confirm the ability of *Salmonella* to deliver DNA or RNA molecules to host cells, HeLa cells were infected at a multiplicity of infection of 100:1 with either wildtype control (bearing to exogenous nucleotides) or 3 strains of *Salmonella* (wildtype, an orgA deletion mutant, and an orgA sifA double deletion mutant) carrying a β-Galactosidase eukaryotic expression plasmid. A 24 hours post-infection, cells were treated with X-Gal. The percentage of cells expressing β-Gal from plasmids delivered by *Salmonella* was determined for each strain. Expression levels for control wildtype *Salmonella* not bearing any plasmid were 0%. Expression of wildtype bacteria delivering the β-Gal plasmid was 12%; delivery of plasmid by the orgA mutant strain resulted in 44% of β-gal positive cells, and delivery by the orgAsifA double mutant yielded 88% of β-gal positive cells.

Example 5

Production of Infectious Exogenous RNA by Bacteria Expressing T7 RNA Polymerase The ability of bacteria to properly express infectious RNA was determined in BL21 *E. coli* expressing T7 RNA polymerase. Bacteria were transformed with plasmids bearing the T7 RNA pol promoter driven cDNAs of either 1) Yellow Fever virus 2) Yellow Fever virus recombinant expressing a Luciferase reporter gene or 3) Yellow Fever virus recombinant expressing the HIV p24 antigen. Expression of T7 RNA polymerase was induced in transformed bacteria and total RNA was extracted from bacteria. This RNA was then electroporated into BHK cells, and the infectiousness of the RNA produced in bacteria was confirmed by the production of Yellow Fever virion using a standard plaque assay as measured in infectious plaque forming units (pfu/ml).

The results are shown in Table 1.

TABLE 1

|  | VIRUS TITER AT x DAYS POST-TRANSFECTION (pfu/ml) | | |
| --- | --- | --- | --- |
|  | 2 days | 3 days | 4 days |
| Yellow Fever RNA | — | — | $4 \times 10^4$ |
| YF-luciferase recombinant | — | — | $5 \times 10^3$ |
| YF-HIVp24 | — | — | $1 \times 10^4$ |

Example 6

Expression of T7 RNA Polymerase in *Salmonella*

Figure 2:
FIG. 2 depicts expression of T7 RNA polymerase in an exemplary bacterial subject delivery system.

To confirm the proper expression of T7 RNA polymerase from the *Salmonella* genome, the T7 RNA polymerase gene was inserted in the place of the asd gene in the orgA and sifA mutant strains. The disruption of the asd gene and its substitution with the T7 RNA pol gene was confirmed by PCR analysis. The results are shown in FIG. 2. Next, the orgA⁻asd⁻T7⁺ (lane 1, 2) and sifA⁻asd⁻T7⁺ (lane 3, 4) strains were cultured in the absence (lane 1, 4) or presence (lane 2, 3) of an inducer, to induce the expression of the T7 RNA polymerase, and expression was confirmed by standard northern blot analysis using a monoclonal anti-T7 RNA polymerase antibody.

Example 7

Oral Administration of *Salmonella* Nucleic Acid Vaccine Carriers

*Salmonella* strains were transformed by electroporation with DNA plasmids encoding β-Galactosidase or poliovirus capsid proteins PV1-4. Transformed bacteria were grown overnight on ampicillin-containing agar plates. Ten positive bacterial colonies were selected and used to launch a 2 ml miniculture of LB broth (with Ampicillin) overnight. A 1/10 dilution of overnight LB culture was used to seed a new 10 ml LB culture containing ampicillin. At an optical density of 0.6, bacterial cultures were gently spun down to pellet, washed 3 times with PBS to remove ampicillin and resuspended in 5 ml of PBS, adjusted to a concentration of approx. $1 \times 10^9$ cfu/ml. Bacterial suspensions were kept on ice.

Eight week old mice were tube-fed 250 microliters of bacterial suspensions using 1 inch rubber tubing fixed to a syringe, permitting deposit of bacteria at the stomach opening.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A bacterial delivery system comprising a live, attenuated bacterium comprising a DNA expression vector, which DNA expression vector comprises a nucleotide sequence encoding an exogenous RNA, wherein the nucleotide sequence is operably linked to a heterologous promoter that is functional in the bacterium, wherein said bacterium synthesizes the exogenous RNA encoded by the DNA vector, wherein the bacterium comprises an asd mutation, resulting in an impaired ability to synthesize a cell wall component, and an orgA mutation, resulting in reduced ability to induce apoptosis in the host eukaryotic cell, wherein the bacterium is a *Salmonella* strain, a *Shigella* strain, an *Eseherichia coli* strain, a *Rickettsia* strain, or a *Listeria* strain, and wherein, following infection of a eukaryotic host cell, the bacterium releases the exogenous RNA into the cytoplasm of the eukaryotic host cell.

2. The system of claim 1, wherein the bacterium is a *Salmonella* strain.

3. The system of claim 1, wherein the promoter is selected from a T7 promoter, a T7/lac promoter, a trc promoter, a tac promoter, a trp promoter, a lac operon promoter, a lac/tac promoter, a tac/trc promoter, a trp/lac promoter, a bad/ara promoter, an ssaG promoter, a pagC promoter, a nirB promoter, a dps promoter, and an spy promoter.

4. The system of claim 1, wherein the bacterium further comprises a nucleic acid that encodes an RNA polymerase that recognizes the heterologous promoter and catalyzes synthesis of RNA encoded by the DNA expression vector.

5. The system of claim 1, wherein the exogenous RNA comprises a nucleotide sequence encoding a polypeptide.

6. The system of claim 5, wherein the polypeptide is an antigen.

7. The system of claim 6, wherein the antigen is selected from a viral antigen, a tumor-associated antigen, a bacterial antigen, and a protozoan antigen.

8. The system of claim 7, wherein said viral antigen is a human immunodeficiency virus antigen.

9. The system of claim 1, wherein the bacterium further comprises an sifA mutation and has reduced retention in a vacuole in a host cell.

10. The system of claim 1, wherein the exogenous RNA is an infectious recombinant viral RNA.

11. The system of claim 1, wherein the exogenous RNA inhibits expression of a target gene present in the eukaryotic host cell.

12. The system of claim 11, wherein the target gene is a viral gene.

13. The system of claim 11, wherein the exogenous RNA is a double-stranded RNA.

14. The system of claim 11, wherein the bacterium further comprises a nucleic acid encoding an endonuclease that cleaves the exogenous RNA.

15. The system of claim 14, wherein the endonuclease is an RNAse III or an RNAse III-like enzyme.

16. A composition comprising the bacterial system of claim 1; and a pharmaceutically acceptable excipient.

17. The composition of claim 16, further comprising an adjuvant.

18. A bacterial delivery system comprising a live, attenuated bacterium comprising a DNA expression vector, which DNA expression vector comprises a nucleotide sequence encoding an exogenous RNA, wherein the exogenous RNA is an infectious recombinant viral RNA, wherein the nucleotide sequence is operably linked to a heterologous promoter that is functional in the bacterium, wherein said bacterium synthesizes the exogenous RNA encoded by the DNA vector, wherein the bacterium is a *Salmonella* strain, a *Shigella* strain, an *Eseherichia coli* strain, a *Rickettsia* strain, or a *Listeria* strain, and wherein, following infection of a eukaryotic host cell, the bacterium releases the exogenous RNA into the cytoplasm of the eukaryotic host cell.

19. The system of claim 18, wherein the bacterium is a *Salmonella* strain.

20. The system of claim 18, wherein the promoter is selected from a T7 promoter, a T7/lac promoter, a trc promoter, a tac promoter, a trp promoter, a lac operon promoter, a lac/tac promoter, a tac/trc promoter, a trp/lac promoter, a bad/ara promoter, an ssaG promoter, a pagC promoter, a nirB promoter, a dps promoter, and an spy promoter.

21. The system of claim 18, wherein the bacterium further comprises a nucleic acid that encodes an RNA polymerase that recognizes the heterologous promoter and catalyzes synthesis of the exogenous RNA encoded by the DNA expression vector.

22. The system of claim 18, wherein the exogenous RNA comprises a nucleotide sequence encoding a heterologous polypeptide.

23. The system of claim 22, wherein the polypeptide is an antigen.

24. The system of claim 23, wherein the antigen is selected from a viral antigen, a tumor-associated antigen, a bacterial antigen, and a protozoan antigen.

25. The system of claim 24, wherein said viral antigen is a human immunodeficiency virus antigen.

26. The system of claim 18, wherein the bacterium comprises one or more mutations selected from a mutation that induces release of the exogenous RNA into the cytoplasm of the host eukaryotic cell, a mutation that reduces the ability of the bacterium to enter into a vacuole in the host eukaryotic cell, a mutation that reduces the ability of the bacterium to induce apoptosis in the host eukaryotic cell, a mutation that reduces the ability of the bacterium to synthesize a bacterial cell wall, and a mutation that reduces the ability of the bacterium to replicate in the host eukaryotic cell.

27. The system of claim 26, wherein the bacterium comprises an asd mutation, and has an impaired ability to synthesize a cell wall component.

28. The system of claim 26, wherein the bacterium comprises an sifA mutation and has reduced retention in a vacuole in a host cell.

29. The system of claim 26, wherein the bacterium comprises an orgA mutation and has a reduced ability to induce apoptosis in the host eukaryotic cell.

30. A composition comprising the bacterial system of claim 18; and a pharmaceutically acceptable excipient.

31. The composition of claim 30, further comprising an adjuvant.

32. The system of claim 1, wherein the bacterium is a *Shigella* strain, an *Escherichia coli* strain, a *Rickettsia* strain, or a *Listeria* strain.

33. The system of claim 18, wherein the bacterium is a *Shigella* strain, an *Eseherichia coli* strain, a *Rickettsia* strain, or a *Listeria* strain.

* * * * *

UNITED STATES PATENT AND TRADEMARK OFFICE
CERTIFICATE OF CORRECTION

| | |
|---|---|
| PATENT NO. | : 7,390,646 B2 |
| APPLICATION NO. | : 10/944256 |
| DATED | : June 24, 2008 |
| INVENTOR(S) | : Derek H. Wells |

Page 1 of 1

It is certified that error appears in the above-identified patent and that said Letters Patent is hereby corrected as shown below:

Col. 1 lines 14-16
"The U.S. government may have certain rights in this invention, pursuant to grant nos. PO1Ai46007 awarded by the National Institutes of Health." should be replaced with -- This invention was made with government support under grant number PO1Ai46007 awarded by the National Institutes of Health. The government has certain rights in the invention. --

Signed and Sealed this

Nineteenth Day of August, 2008

JON W. DUDAS
*Director of the United States Patent and Trademark Office*

UNITED STATES PATENT AND TRADEMARK OFFICE
CERTIFICATE OF CORRECTION

PATENT NO. : 7,390,646 B2  Page 1 of 1
APPLICATION NO. : 10/944256
DATED : June 24, 2008
INVENTOR(S) : Andino-Pavlovsky et al.

It is certified that error appears in the above-identified patent and that said Letters Patent is hereby corrected as shown below:

Claim 1, column 40, line 49: Delete "Eseherichia" and replace it with "Escherichia".
Claim 3, column 40, line 61: Delete "spy" and replace it with "spv".
Claim 18, column 41, line 38: Delete "Eseherichia" and replace it with "Escherichia".
Claim 20, column 42, line 2: Delete "spy" and replace it with "spv".

Signed and Sealed this

Seventh Day of July, 2009

JOHN DOLL
*Acting Director of the United States Patent and Trademark Office*